US010561489B2

(12) United States Patent
Okumura et al.

(10) Patent No.: US 10,561,489 B2
(45) Date of Patent: Feb. 18, 2020

(54) GASTROINTESTINAL-TRACT CONSTRICTING METHOD

(71) Applicant: OLYMPUS CORPORATION, Tokyo (JP)

(72) Inventors: Takuya Okumura, Tokyo (JP); Shunsuke Motosugi, Tokyo (JP); Takayuki Hatanaka, Tokyo (JP); Hiroyuki Morishita, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 115 days.

(21) Appl. No.: 15/911,230

(22) Filed: Mar. 5, 2018

(65) Prior Publication Data

US 2019/0269493 A1  Sep. 5, 2019

(51) Int. Cl.
*A61F 2/04* (2013.01)
*A61B 1/273* (2006.01)

(52) U.S. Cl.
CPC ............... *A61F 2/04* (2013.01); *A61B 1/2736* (2013.01); *A61F 2002/044* (2013.01); *A61F 2002/045* (2013.01)

(58) Field of Classification Search
CPC ............ A61F 2/04; A61B 2017/00827; A61M 2005/31523
USPC ...................................................... 623/23.65
See application file for complete search history.

(56) References Cited

U.S. PATENT DOCUMENTS

| 5,645,560 | A | 7/1997 | Crocker et al. |
| 5,843,116 | A | 12/1998 | Crocker et al. |
| 6,027,486 | A | 2/2000 | Crocker et al. |
| 6,098,629 | A | 8/2000 | Johnson et al. |
| 6,338,345 | B1 | 1/2002 | Johnson et al. |
| 6,401,718 | B1 | 6/2002 | Johnson et al. |
| 6,488,653 | B1 | 12/2002 | Lombardo |
| 6,500,174 | B1 | 12/2002 | Maguire et al. |
| 6,544,226 | B1 | 4/2003 | Gaiser et al. |
| 7,185,657 | B1 | 3/2007 | Johnson et al. |

(Continued)

FOREIGN PATENT DOCUMENTS

| EP | 2 298 250 A1 | 3/2011 |
| EP | 3 141 192 A1 | 3/2017 |

(Continued)

OTHER PUBLICATIONS

Office Action dated Sep. 9, 2019 received in U.S. Appl. No. 15/942,617.

*Primary Examiner* — Suzette J Gherbi
(74) *Attorney, Agent, or Firm* — Scully, Scott, Murphy & Presser, P.C.

(57) ABSTRACT

A gastrointestinal-tract constricting method includes: while observing the gastrointestinal tract by inserting an endoscope into the gastrointestinal tract, forming a spreading block that suppresses infiltration of a substance, which damages a mucosa basal layer of the gastrointestinal tract, into the muscular layer underlying the mucosa basal layer, the spreading block being formed along a circumferential direction of the gastrointestinal tract and between the mucosa basal layer and the muscular layer; and supplying the substance to a gap between the spreading block and the mucosa basal layer while forming a contact surface between the spreading block and the substance along the circumferential direction of the gastrointestinal tract.

11 Claims, 17 Drawing Sheets

(56) References Cited

U.S. PATENT DOCUMENTS

| | | |
|---|---|---|
| 2002/0148475 A1 | 10/2002 | Johnson et al. |
| 2002/0198521 A1 | 12/2002 | Maguire |
| 2003/0183962 A1 | 10/2003 | Buiser et al. |
| 2003/0233150 A1 | 12/2003 | Bourne et al. |
| 2003/0236535 A1 | 12/2003 | Onuki et al. |
| 2004/0087936 A1 | 5/2004 | Stern et al. |
| 2005/0096673 A1 | 5/2005 | Stack et al. |
| 2005/0247320 A1 | 11/2005 | Stack et al. |
| 2006/0247610 A1 | 11/2006 | Lanphere et al. |
| 2007/0060932 A1 | 3/2007 | Stack et al. |
| 2007/0135822 A1 | 6/2007 | Onuki et al. |
| 2007/0260112 A1 | 11/2007 | Rahmani |
| 2007/0260178 A1 | 11/2007 | Skerven et al. |
| 2007/0276432 A1 | 11/2007 | Stack et al. |
| 2008/0015523 A1 | 1/2008 | Baker et al. |
| 2008/0065122 A1 | 3/2008 | Stack et al. |
| 2009/0018602 A1 | 1/2009 | Mitelberg et al. |
| 2010/0168512 A1 | 7/2010 | Rahmani |
| 2010/0174306 A1 | 7/2010 | Mitelberg et al. |
| 2010/0217151 A1 | 8/2010 | Gostout et al. |
| 2010/0241146 A1 | 9/2010 | Stack et al. |
| 2011/0257622 A1 | 10/2011 | Salahieh et al. |
| 2012/0095395 A1 | 4/2012 | Haery |
| 2012/0226300 A1 | 9/2012 | Mitelberg et al. |
| 2012/0226302 A1 | 9/2012 | Mitelberg et al. |
| 2013/0012863 A1 | 1/2013 | Stack et al. |
| 2013/0197554 A1 | 8/2013 | Skerven et al. |
| 2013/0345670 A1 | 12/2013 | Rajagopalan et al. |
| 2014/0010847 A1 | 1/2014 | Lin |
| 2014/0121585 A1 | 5/2014 | Baker et al. |
| 2014/0249465 A1 | 9/2014 | Stack et al. |
| 2015/0025313 A1* | 1/2015 | Baker ................. A61F 2/95 600/104 |
| 2015/0032087 A1 | 1/2015 | Shibata et al. |
| 2015/0157358 A1* | 6/2015 | Mitelberg ............. A61B 10/02 606/46 |
| 2015/0164670 A1* | 6/2015 | Silverman ........ A61B 17/00234 606/157 |
| 2015/0352334 A1 | 12/2015 | Haery |
| 2015/0374352 A1 | 12/2015 | Inoue |
| 2016/0015855 A1* | 1/2016 | Nohara ................. A61K 38/00 514/13.5 |
| 2016/0213890 A1 | 7/2016 | Kaufman et al. |
| 2016/0262867 A1 | 9/2016 | Baker et al. |
| 2016/0278662 A1* | 9/2016 | Brister ................. A61B 5/6853 |
| 2016/0296675 A1 | 10/2016 | Longo et al. |
| 2016/0310200 A1 | 10/2016 | Wang |
| 2017/0035595 A1 | 2/2017 | Stack et al. |
| 2018/0015264 A1 | 1/2018 | Wang et al. |
| 2018/0296511 A1* | 10/2018 | Bannister ................. A61K 9/08 |
| 2018/0296806 A1 | 10/2018 | Haery |
| 2019/0038881 A1 | 2/2019 | Wang et al. |
| 2019/0076283 A1* | 3/2019 | Okumura ............. A61B 18/082 |
| 2019/0247390 A1* | 8/2019 | Gedulin ............... A61K 9/0031 |

FOREIGN PATENT DOCUMENTS

| | | |
|---|---|---|
| JP | 2000-509304 A | 7/2000 |
| JP | 2002-538932 A | 11/2002 |
| JP | 2002-540838 A | 12/2002 |
| JP | 2003-507096 A | 2/2003 |
| JP | 2003-526460 A | 9/2003 |
| JP | 2004-000601 A | 1/2004 |
| JP | 2005-521476 A | 7/2005 |
| JP | 2007-508053 A | 4/2007 |
| JP | 2008-526461 A | 7/2008 |
| JP | 2009-533150 A | 9/2009 |
| JP | 2009-536083 A | 10/2009 |
| JP | 2010-533036 A | 10/2010 |
| JP | 2014-508580 A | 4/2014 |
| JP | 2014-521390 A | 8/2014 |
| JP | 2014-171629 A | 9/2014 |
| JP | 2014-188205 A | 10/2014 |
| JP | 2015-023904 A | 2/2015 |
| JP | 2015-033634 A | 2/2015 |
| JP | 2015-066144 A | 4/2015 |
| JP | 2016-032523 A | 3/2016 |
| JP | 2016-154927 A | 9/2016 |
| JP | 2016-185296 A | 10/2016 |
| JP | 2017-533036 A | 11/2017 |
| JP | 2018-504209 A | 2/2018 |
| WO | 1997/40877 A1 | 11/1997 |
| WO | 2000/56237 A2 | 9/2000 |
| WO | 00/59398 A1 | 10/2000 |
| WO | 2001/012255 A1 | 2/2001 |
| WO | 01/68015 A1 | 9/2001 |
| WO | 03/082359 A1 | 10/2003 |
| WO | 2005/037152 A1 | 4/2005 |
| WO | 2006/078672 A1 | 7/2006 |
| WO | 2007/120727 A1 | 10/2007 |
| WO | 2007/131112 A2 | 11/2007 |
| WO | 2009/009274 A2 | 1/2009 |
| WO | 2012/054387 A2 | 4/2012 |
| WO | 2012/099974 A2 | 7/2012 |
| WO | 2012/162114 A1 | 11/2012 |
| WO | 2015/016162 A1 | 2/2015 |
| WO | 2016/070032 A1 | 5/2016 |
| WO | 2016/118923 A1 | 7/2016 |
| WO | 2016/158290 A1 | 10/2016 |

* cited by examiner

GASTROINTESTINAL-TRACT CONSTRICTING METHOD

TECHNICAL FIELD

The present invention relates to a gastrointestinal-tract constricting method.

BACKGROUND ART

Heretofore, known methods for treating gastroesophageal reflux disease, which is a benign disorder caused by degradation of the function of the cardiac sphincter at the entrance of the stomach, include oral administration of a proton pump inhibitor (PPI) that decreases the amount of gastric acid, the Nissen fundoplication technique (fundoplication technique) that involves wrapping a part of the stomach around the esophagus, the LINX technique that involves squeezing the esophagus with a magnet band or rubber band, the transoral incisionless fundoplication (TIF) technique that involves pulling the cardiac part under peroral endoscopy and stapling the cardiac part in the pulled state to form a valve, etc.

In addition, the methods described in, for example, PTL 1 and PTL 2 are known as other methods for treating gastroesophageal reflux disease. The method described in PTL 1 involves removing tissue from the surface of a gastrointestinal tract, such as the esophagus, the stomach, or the like, and re-constructing the body passageway by utilizing the healing reaction. In PTL 2 , the gastrointestinal tract is constricted by deliberately causing scars to form by incising at least one of the mucosal layer and the submucosal layer in the gastroesophageal junction or the stomach.

CITATION LIST

Patent Literature

{PTL 1} Japanese Translation of PCT International Application, Publication No. 2009-536083
{PTL 2} US Patent Application No. 2015/0374352

SUMMARY OF INVENTION

One aspect of the present invention provides a gastrointestinal-tract constricting method comprising: while observing the gastrointestinal tract by inserting an endoscope into the gastrointestinal tract, forming a spreading block that blocks infiltration of a substance, which damages a mucosa basal layer of the gastrointestinal tract, into the muscular layer underlying the mucosa basal layer, the spreading block being formed along a circumferential direction of the gastrointestinal tract and between the mucosa basal layer and the muscular layer; and supplying the substance to a gap between the spreading block and the mucosa basal layer while forming a contact surface between the spreading block and the substance along the circumferential direction of the gastrointestinal tract.

DESCRIPTION OF EMBODIMENTS

First Embodiment

A gastrointestinal-tract constricting method according to a first embodiment of the present invention will now be described with reference to the drawings.

Figure 1:
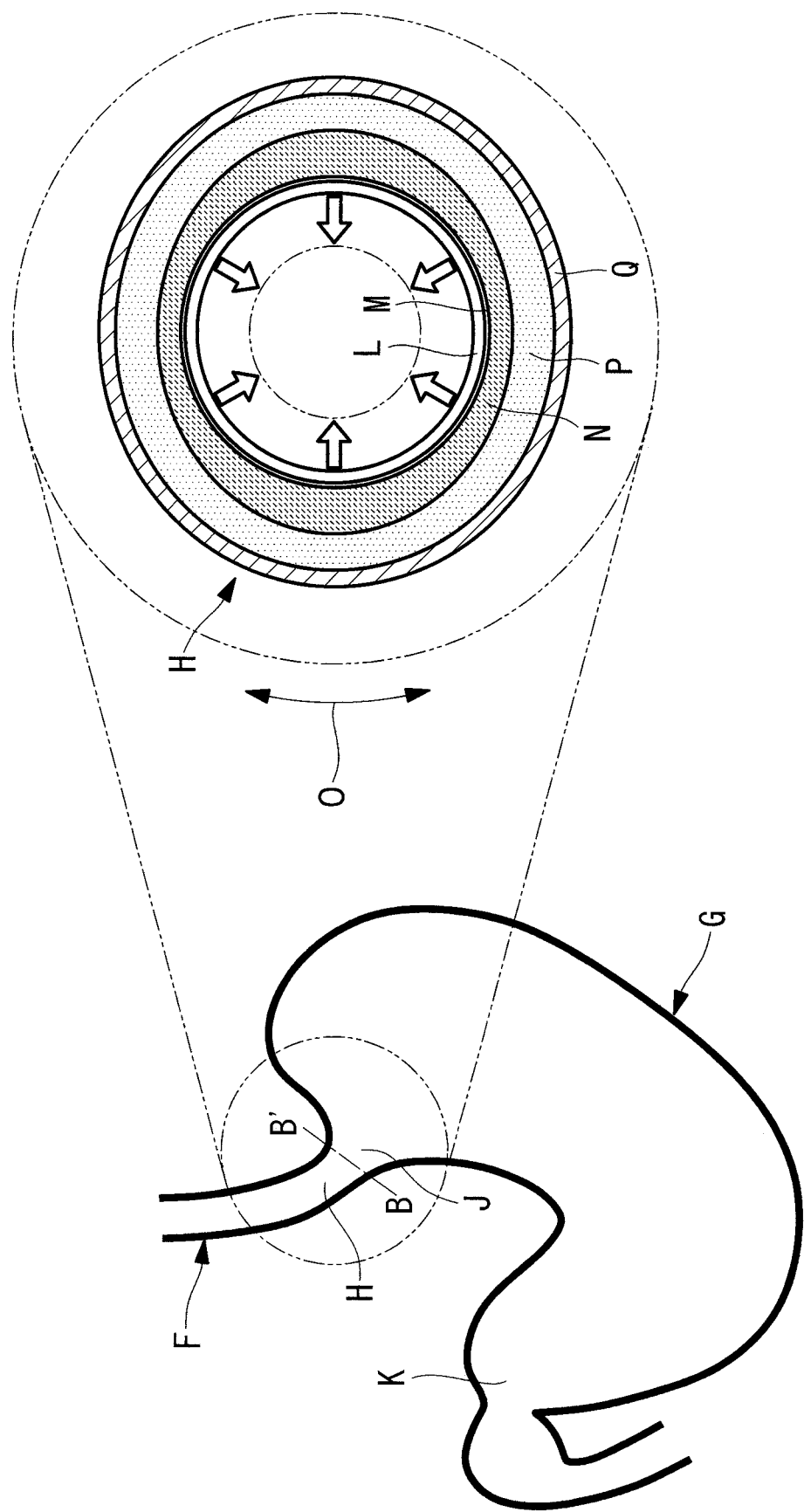
FIG. 1 includes a diagram illustrating the periphery of the gastroesophageal junction to which a gastrointestinal-tract constricting method according to a first embodiment of the present invention is applied, and a cross-sectional view taken along B-B' illustrating a transverse section of the gastroesophageal junction.

The case described as an example in this embodiment is the case in which the gastrointestinal-tract constricting method is applied to the treatment of gastroesophageal reflux disease, wherein, as illustrated in FIG. 1, a part of a region that extends from the gastroesophageal junction H (lower part of the esophagus), where the esophagus F connects to the stomach G, to the cardiac part is constricted. In FIG. 1, reference sign J denotes the cardiac part constituting the entrance of the stomach G, reference sign K denotes the pyloric part constituting the endmost part of the stomach G, reference sign L denotes the mucosal layer, reference sign M denotes the mucosa basal layer, reference sign N denotes the submucosal layer, reference sign P denotes the muscular layer, and reference sign Q denotes the serosa.

Figure 2:
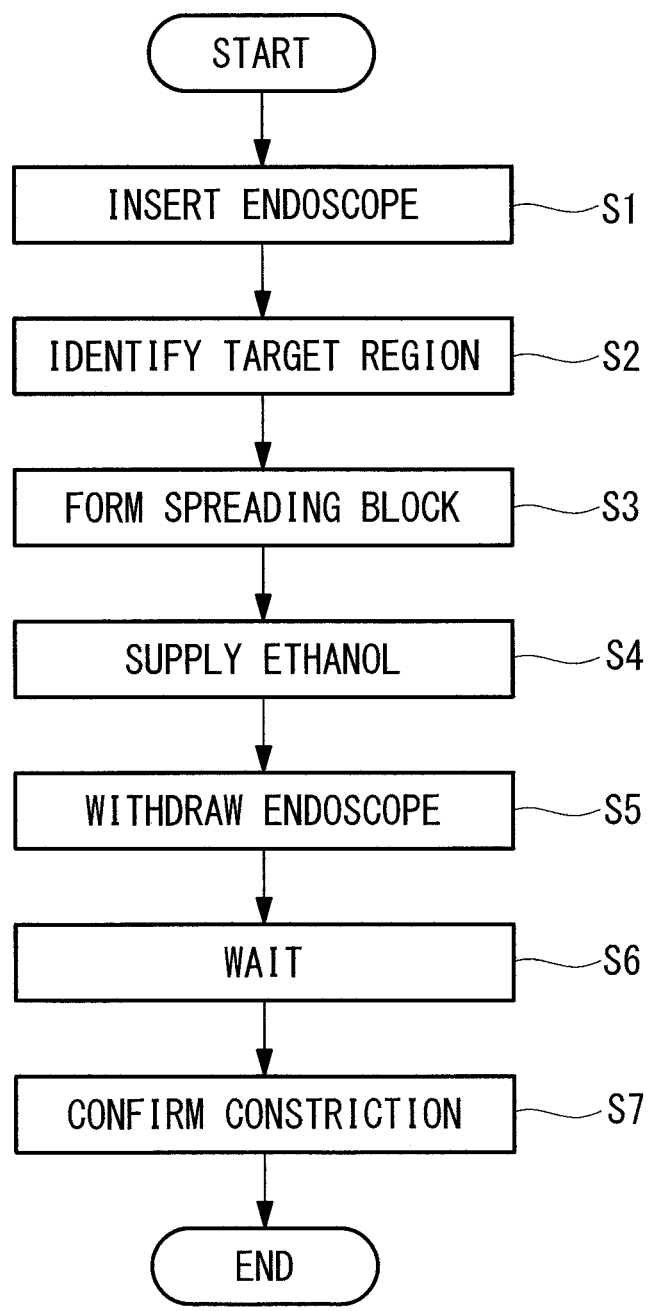
FIG. 2 is a flowchart illustrating the gastrointestinal-tract constricting method according to the first embodiment of the present invention.

As illustrated in the flowchart of FIG. 2, the gastrointestinal-tract constricting method includes an inserting step S1 of inserting an endoscope into the gastrointestinal tract constituting the gastroesophageal junction H; an identifying step S2 of identifying a target region where the tissue located between the mucosal layer L and the muscular layer P in the gastroesophageal junction H is to be damaged by ethanol (substance) while observing the gastroesophageal junction H with an endoscope; a block forming step S3 of forming a spreading block that blocks the infiltration of ethanol, which is to be supplied to the target region, into the muscular layer P or into a radially outer side (abdominal cavity side) of the gastrointestinal tract with respect to the muscular layer P; a supplying step S4 of supplying ethanol to the target region after the block forming step S3; an endoscope withdrawing step S5 of withdrawing an endoscope 1 from the inside of the gastrointestinal tract to the outside of the body; a waiting step S6 of waiting until a part of the region extending from the gastroesophageal junction H (lower part of the esophagus) to the cardiac part is constricted; and a constriction confirming step S7 of confirming constriction of the part of the region extending from the gastroesophageal junction H (lower part of the esophagus) to the cardiac part.

Figure 3:
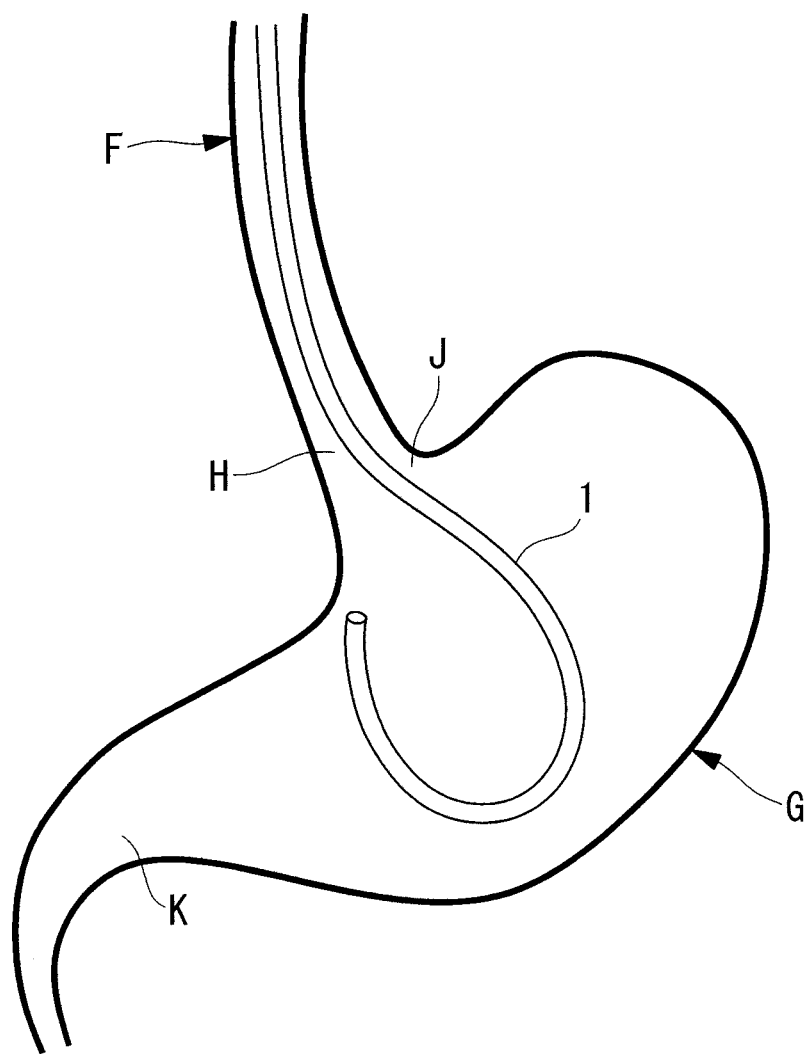
FIG. 3 is a longitudinal sectional view showing how an endoscope is inserted into the stomach illustrated in FIG. 1.

As illustrated in FIG. 3, in the inserting step S1, the endoscope 1 is inserted via the mouth of a subject into the stomach G through the esophagus F, the distal end of the endoscope 1 is bent inside the stomach G, and the distal end of the endoscope 1 is arranged to face the cardiac part J and the gastroesophageal junction H as if to look up into the esophagus F from the stomach G.

Figure 4:
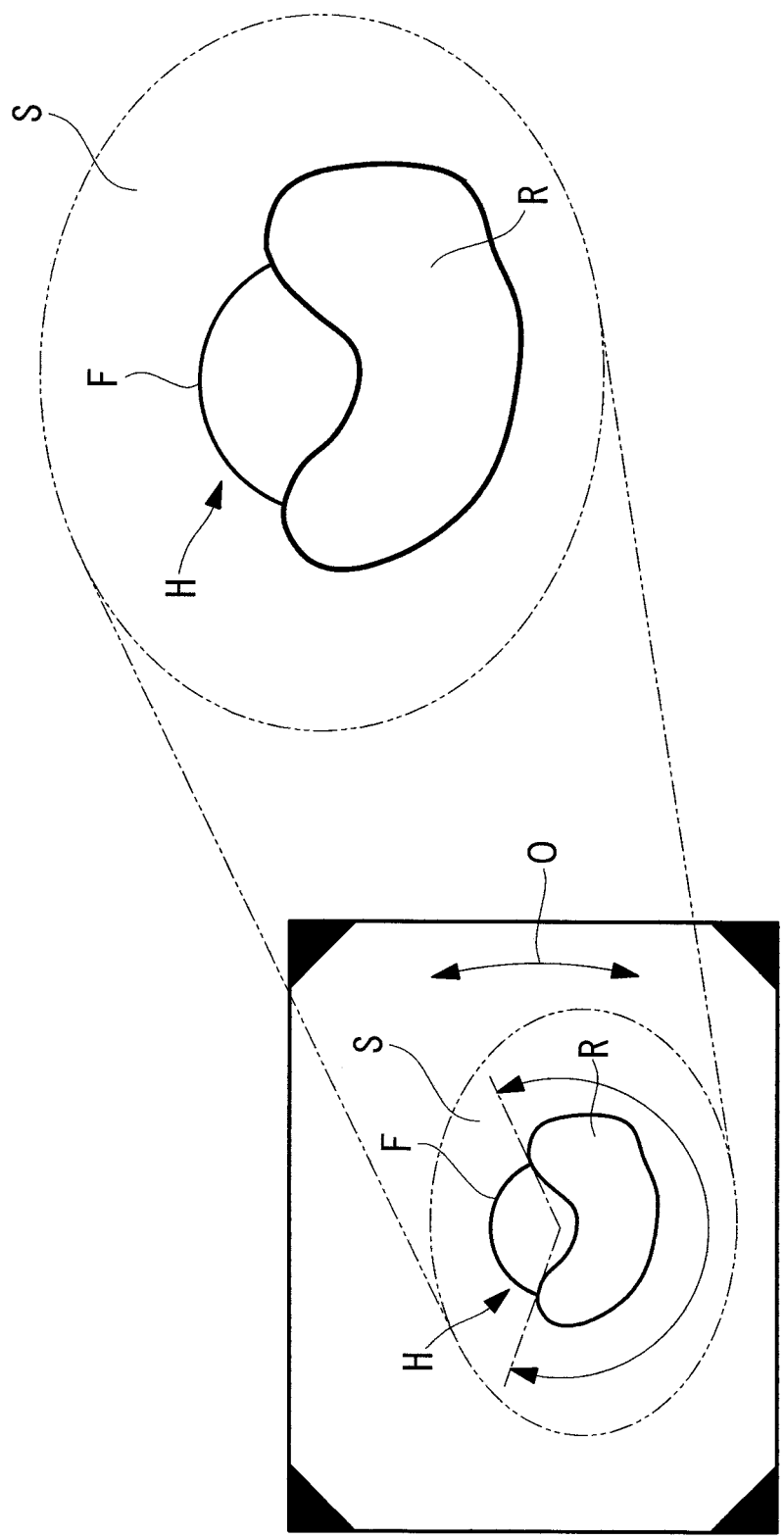
FIG. 4 is an endoscopic image of the gastroesophageal junction illustrated in FIG. 1 and a mucosal surface in a target region, as viewed from the inside of the stomach.

As illustrated in FIG. 4, in the identifying step S2, after observation of the mucosal surface of the relaxed cardiac part J with the endoscope 1, the range of a target region R on the surface of the mucosal layer L is identified. In FIG. 4, reference sign S denotes the gastric wall; and in FIGS. 1 and 4, the arrow indicated by reference sign O indicates the circumferential direction of the gastrointestinal tract.

In the supplying step S4 described below, in the range coincident with the thus identified target region R, the mucosa basal layer M (refer to FIG. 1), which is the lowermost layer of the mucosal layer L, in a part of the region extending from the gastroesophageal junction H (lower part of the esophagus) to the cardiac part J is damaged. By damaging the mucosa basal layer M in the target region R, constriction occurs in part of the region extending from the gastroesophageal junction H (lower part of the esophagus) to the cardiac part J. Preferably, the range of the target region R is appropriately determined in advance for the purposes of adjusting the inner diameter of the lumen after constriction to a desired inner diameter in the gastroesophageal junction H.

Figure 5:
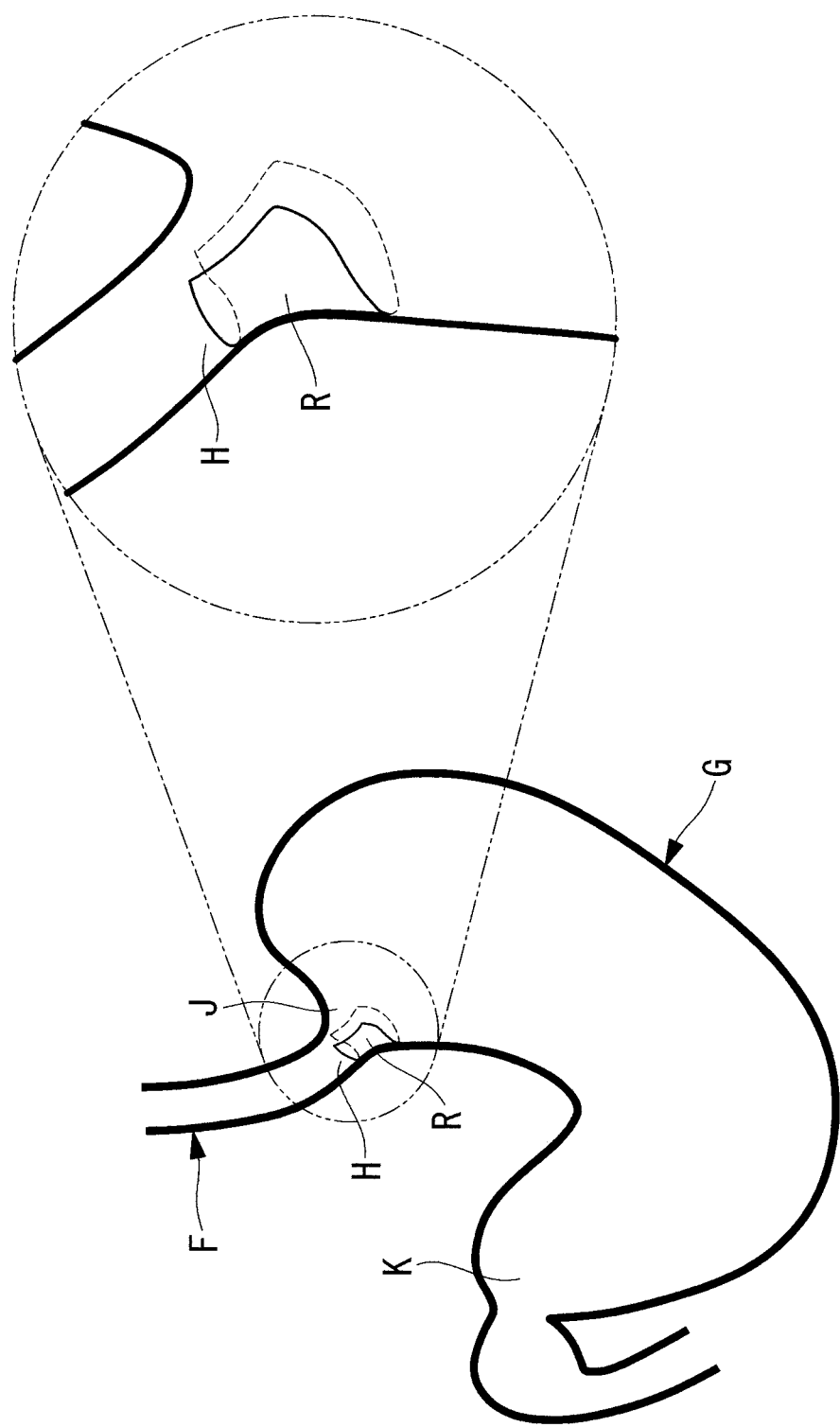
FIG. 5 is a diagram illustrating the position of the target region in the gastroesophageal junction.
Figure 6:
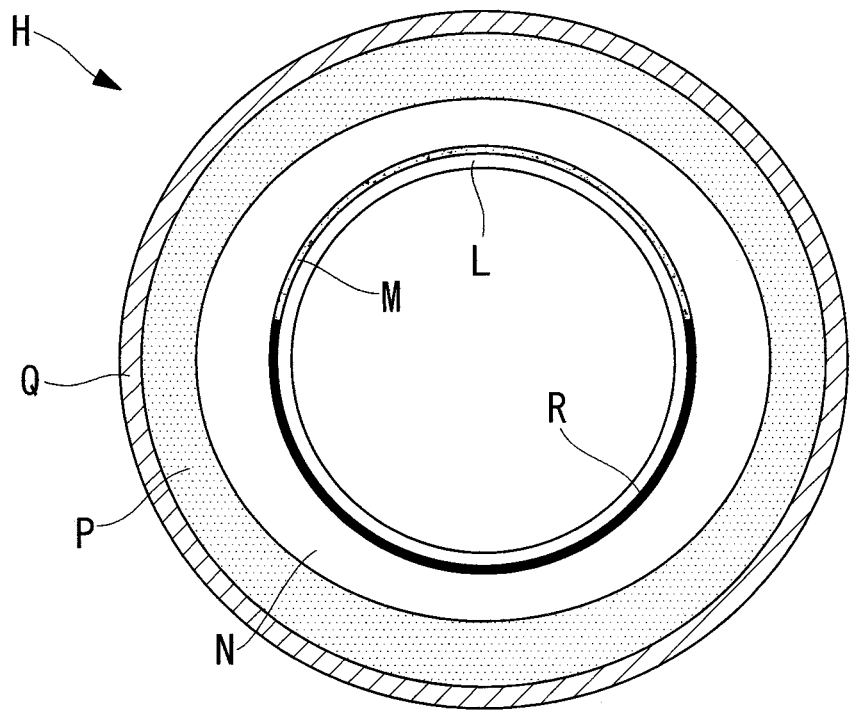
FIG. 6 is a cross-sectional view of the gastroesophageal junction taken along B-B' in FIG. 1, and illustrates the position of the target region.

In order to prevent excessive constriction, the target region R is set to be a part of the region extending from the gastroesophageal junction H (lower part of the esophagus) to the cardiac part J, and is a range that does not extend all around the circumference. For example, as illustrated in FIGS. 5 and 6, the target region R is preferably a range that extends from the lesser curvature side to the gastric fundus side and occupies 60% to 80% of the entire circumference.

Figure 7:
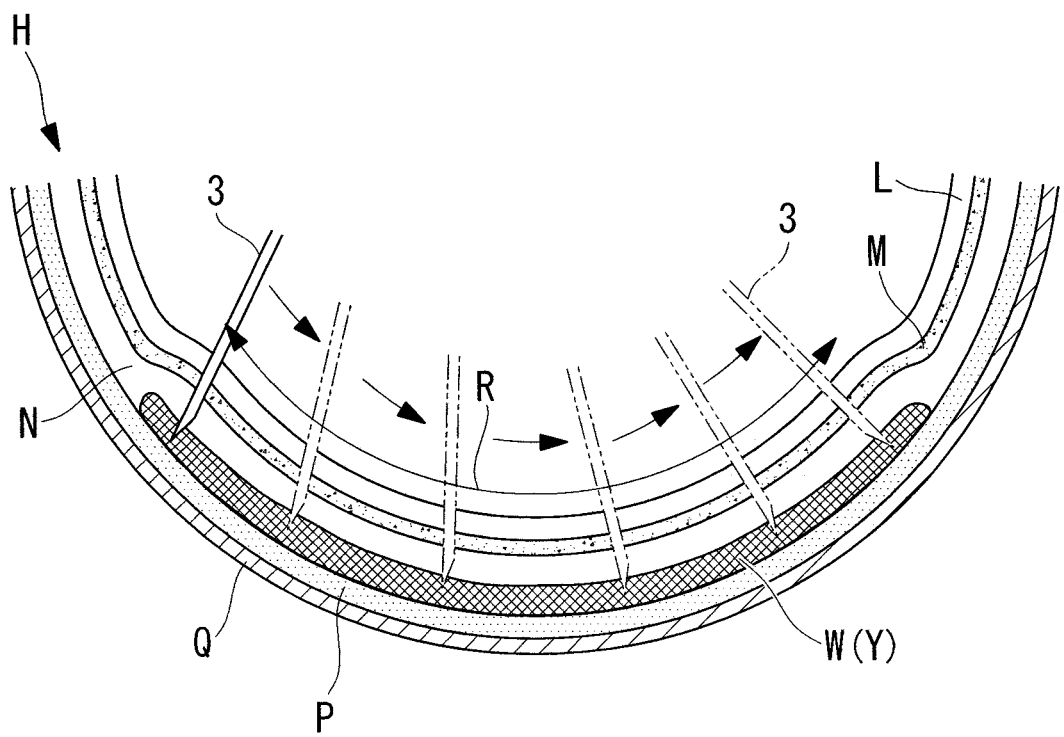
FIG. 7 is a partial cross-sectional view taken along B-B' in FIG. 1, and illustrates how a spreading block is formed by injecting a sodium hyaluronate solution into the submucosal layer.

In the block forming step S3, as illustrated in FIG. 7, a spreading block W is formed in the submucosal layer (position between the mucosal layer L and the muscular layer P) N in the target region R by using an infiltration inhibitor that suppresses infiltration of ethanol. As the infiltration inhibitor, for example, a sodium hyaluronate solution, which is a liquid that is immiscible with ethanol due to substance polarity and that has a higher viscosity than ethanol, is used.

As illustrated in FIG. 7, in the block forming step S3, an injection needle 3 of an injection-needle-equipped treatment tool is used to fill the submucosal layer N in the target region R with the sodium hyaluronate solution Y so as to form a spreading block W composed of the sodium hyaluronate solution Y in the submucosal layer N. The sodium hyaluronate solution Y can remain at the injected position in the submucosal layer N due to its high viscosity. The spreading block W has, for example, a shape such that at least part of the transverse section thereof extends in an arc shape along the circumferential direction of the gastrointestinal tract.

Furthermore, the spreading block W is preferably formed over a range larger than the target region R in the circumferential direction and the longitudinal direction of the gastrointestinal tract. When the spreading block W is formed over a range larger than the target region R in the circumferential direction and the longitudinal direction of the gastrointestinal tract, it is possible to more reliably suppress infiltration of ethanol Z, which is supplied to the target region R and circumvents the spreading block W from the outer side in the circumferential direction of the gastrointestinal tract, into the muscular layer P. In the longitudinal direction (direction along the axial line) of the gastrointestinal tract, the spreading block W is preferably formed partly in the region that extends from the gastroesophageal junction H (lower part of the esophagus) to the cardiac part J.

Figure 8:
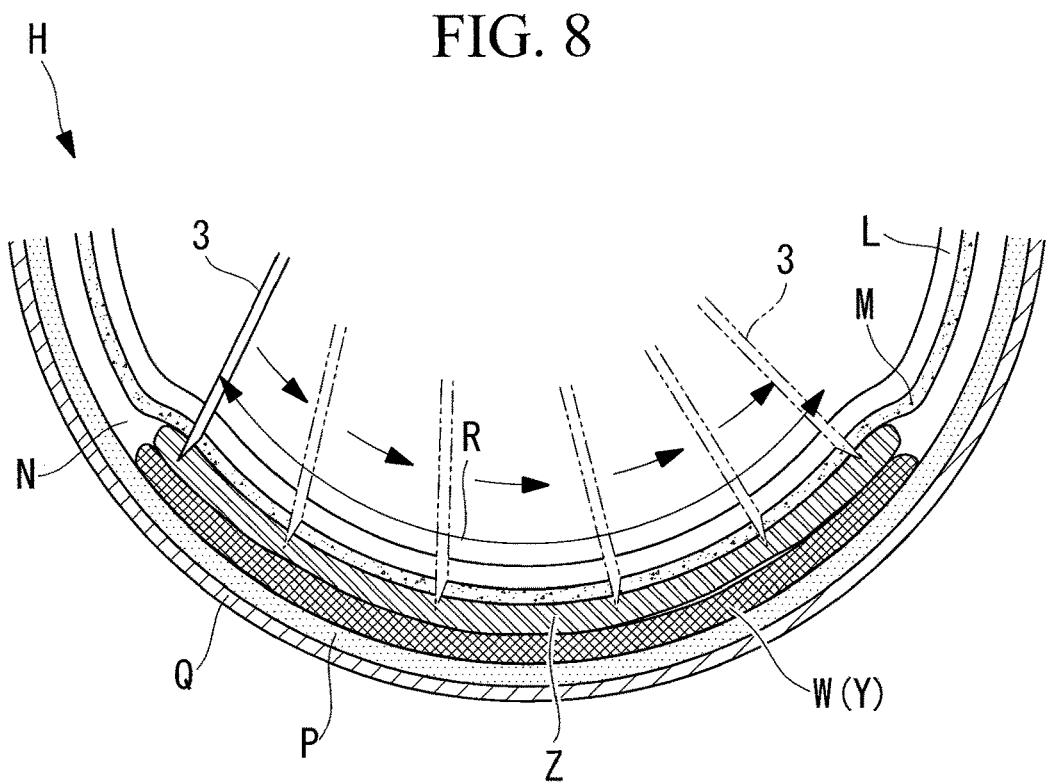
FIG. 8 is a partial cross-sectional view of the gastroesophageal junction taken along B-B' in FIG. 1, and illustrates how ethanol is injected between the spreading block and the mucosa basal layer.

As illustrated in FIG. 8, in the supplying step S4, an injection needle 3 of the injection-needle-equipped treatment tool is used to inject ethanol Z between the mucosa basal layer M and the spreading block W while forming a contact surface between the spreading block W and the ethanol Z along the circumferential direction of the gastrointestinal tract in the target region (for example, the gastroesophageal junction H). Note that the mucosa basal layer M in the target region R lies on the inner side of the gastrointestinal tract with respect to the spreading block W, in other words, lies on the radially inner side of the gastrointestinal tract with respect to the spreading block W.

The effects of the gastrointestinal-tract constricting method according to this embodiment will now be described.

In order to constrict a part of the region extending from the gastroesophageal junction H (lower part of the esophagus) to the cardiac part J of the subject by the gastrointestinal-tract constricting method according to this embodiment, first, as illustrated in FIG. 3, the endoscope 1 is inserted into the gastrointestinal tract via the mouth of the subject, and the distal end of the endoscope 1 is bent inside the stomach G so as to face the cardiac part J and the gastroesophageal junction H (inserting step S1).

Next, as illustrated in FIGS. 4, 5, and 6, while observing the region that extends from the gastroesophageal junction H (lower part of the esophagus) to the cardiac part J with the endoscope 1, the target region R is identified in the region that extends from the gastroesophageal junction H (lower part of the esophagus) to the cardiac part J (identifying step S2).

Once the target region R is identified, the injection-needle-equipped treatment tool (not illustrated) is inserted into a forceps channel of the endoscope 1, and a syringe (not illustrated) filled with the sodium hyaluronate solution Y is attached to the injection-needle-equipped treatment tool.

Then, as illustrated in FIG. 7, an injection needle 3 of the injection-needle-equipped treatment tool punctures the submucosal layer N in the target region R, and the sodium hyaluronate solution Y is injected into the submucosal layer N. This operation is repeated several times by shifting the position in the circumferential direction of the gastrointestinal tract that constitutes the target region (for example, the gastroesophageal junction H) so as to form a spreading block W in the submucosal layer N in the target region R, the spreading block W spanning over a range larger than the target region R in the circumferential direction of the gastroesophageal junction H and being filled with the sodium hyaluronate solution Y (block forming step S3).

After the spreading block W is formed, a syringe (not illustrated) filled with ethanol is attached to the injection-needle-equipped treatment tool so as to replace the syringe filled with the sodium hyaluronate solution Y. Next, as illustrated in FIG. 8, the target region R is punctured with the injection needle 3 of the injection-needle-equipped treatment tool so as to inject the ethanol Z between the mucosa basal layer M and the spreading block W in the target region R. This operation is repeated several times while shifting the position in the circumferential direction of the gastrointestinal tract within the target region R so that the ethanol Z spreads evenly between the mucosa basal layer M and the spreading block W and throughout the target region R (supplying step S4).

As a result, the ethanol Z infiltrates into the opposite side (inner side of the gastrointestinal tract) from the spreading block W through the gap between the mucosa basal layer M and the spreading block W in the target region R, and thus at least the mucosa basal layer M in the target region R becomes damaged by the ethanol Z. The range in which the ethanol Z is injected between the mucosa basal layer M and the spreading block W can be confirmed by the position of the protrusion on the surface of the mucosa layer L. The ethanol Z reaches the mucosa basal layer M and damages the mucosa basal layer M before it is absorbed in the body. In other words, the ethanol Z is absorbed in the body after causing damage to the mucosa basal layer M. The sodium hyaluronate solution Y is absorbed in the body more slowly than the ethanol Z is. Thus, the state in which the spreading block W is formed is maintained until the ethanol Z is absorbed in the body.

After the supplying step S4, whether the ethanol Z has been supplied between the mucosa basal layer M and the spreading block W in the target region R is confirmed, and then the endoscope 1 is withdrawn out of the body from the gastrointestinal tract (endoscope withdrawing step S5).

After the endoscope 1 is withdrawn out of the body from the gastrointestinal tract, the operation thereof is waited until the part of the region extending from the gastroesophageal junction H (lower part of the esophagus) to the cardiac part J is constricted by the constrictive effect of the tissue around the target region R undergoing the process of forming scars as the damaged tissue heals (waiting step S6).

After waiting of the operation until the part of the region extending from the gastroesophageal junction H (lower part of the esophagus) to the cardiac part J is constricted, the endoscope 1 is again inserted into the gastrointestinal tract so as to confirm that the part of the region extending from the gastroesophageal junction H (lower part of the esophagus) to the cardiac part J is constricted (constriction confirming step S7). The gastric acid reflux can be suppressed without excessively constricting a part of the region that extends from the gastroesophageal junction H (lower part of the esophagus) to the cardiac part J by constricting the part of the region that extends from the gastroesophageal junction H (lower part of the esophagus) to the cardiac part J by damaging the mucosa basal layer M with the ethanol Z within the range of the desired target region R, which is a part of the region extending from the gastroesophageal junction H (lower part of the esophagus) to the cardiac part J and which does not extend all around the circumference.

If needed, after the sodium hyaluronate solution Y is injected into the submucosal layer N as described in the block forming step S3, the ethanol Z may be additionally injected between mucosa basal layer M and the spreading block W, as described in the supplying step S4.

As described above, according to the gastrointestinal-tract constricting method of this embodiment, since the mucosa basal layer M in the target region R (for example, the gastroesophageal junction) is damaged by the ethanol Z, the invasiveness is low and the procedure is simple compared to when the tissue is damaged by incising the target region R (for example, the gastroesophageal junction H) or excising the tissue in the target region R.

Figure 9:
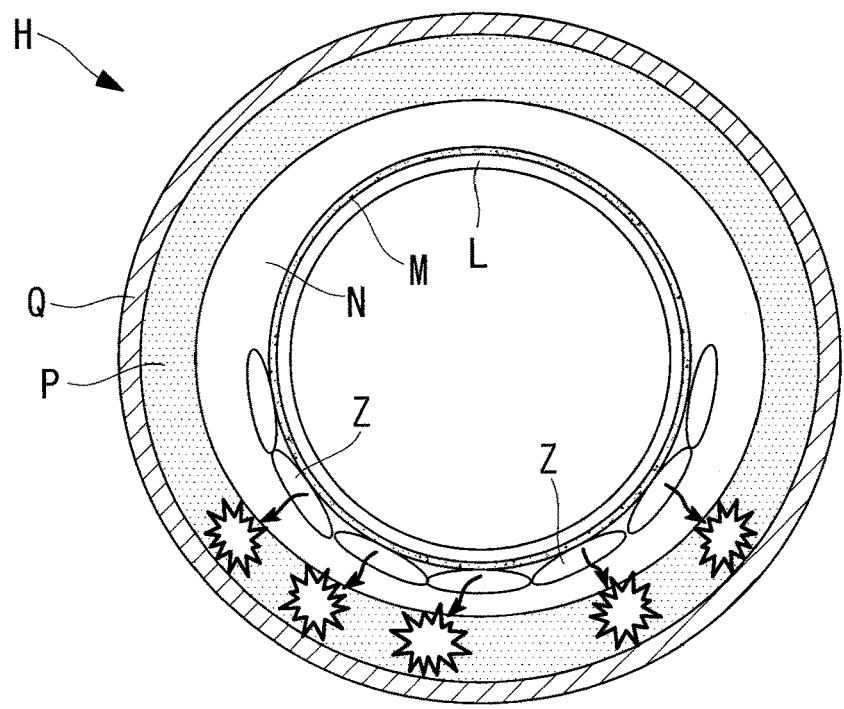
FIG. 9 is a cross-sectional view of the gastroesophageal junction taken along B-B' in FIG. 1, and illustrates how ethanol infiltrates into the outer side of the submucosal layer when the spreading block is not formed.

In such a case, if no spreading block W is provided between the mucosa layer L and the muscular layer P in the target region R, as illustrated in FIG. 9, the ethanol Z injected into the submucosal layer N in the target region R infiltrates into the muscular layer P (the muscular layer P underlying the mucosa basal layer M) on the radially outer side of the gastrointestinal tract with respect to the submucosal layer N and into the radially outer side (abdominal cavity side) of the gastrointestinal tract with respect to the muscular layer P; thus, the muscular layer P may become damaged, possibly resulting in perforation and bleeding.

Figure 10:
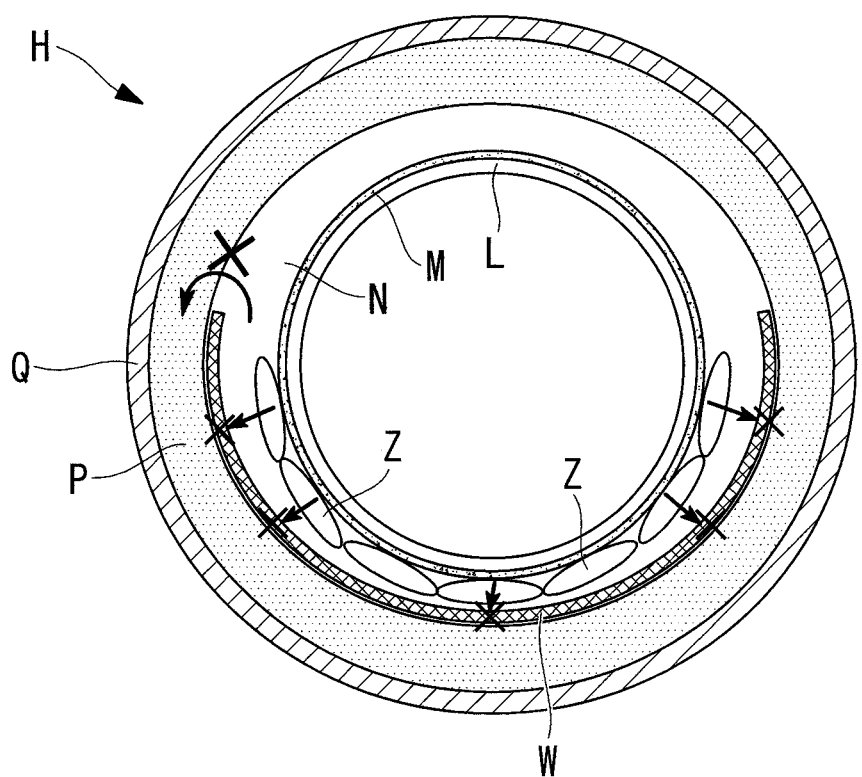
FIG. 10 is a cross-sectional view of the gastroesophageal junction taken along B-B' in FIG. 1, and illustrates how the spreading block suppresses infiltration of ethanol into the outer side of the submucosal layer.

To address this issue, as illustrated in FIG. 10, the spreading block W is formed in advance between the mucosa basal layer M and the muscular layer P in the target region R. Subsequently, by injecting the ethanol Z into the gap between the spreading block W and the mucosa basal layer M in the gastroesophageal junction H, the ethanol Z infiltrates toward the radially outer side of the gastrointestinal tract but is blocked by the spreading block W. As a result, the ethanol Z stays at a position between the mucosal layer L and the muscular layer P, and, at the same time, infiltration of the ethanol Z into the muscular layer P and the radially outer side (abdominal cavity side) of the gastrointestinal tract with respect to the muscular layer P can be suppressed.

Thus, a part of the region extending from the gastroesophageal junction H (lower part of the esophagus) to the cardiac part J can be constricted by causing the constrictive effect to occur in the tissue in the mucosa basal layer M without damaging the muscular layer P.

In this embodiment, the spreading block W is formed partly in the circumferential direction of the gastrointestinal tract; alternatively, the spreading block W may be formed all around the circumference of the gastrointestinal tract by supplying sodium hyaluronate.

Moreover, in this embodiment, the spreading block W is formed by injecting the sodium hyaluronate solution Y into the submucosal layer N in the target region R (for example, the gastroesophageal junction H); alternatively, for example, the spreading block W may be formed by placing an absorbent polymer in the submucosal layer N in the target region R. In this case also, since the absorbent polymer absorbs the ethanol Z, infiltration of the ethanol Z into the muscular layer P and the radially outer side (abdominal cavity side) of the gastrointestinal tract with respect to the muscular layer P can be suppressed.

Second Embodiment

A gastrointestinal-tract constricting method according to a second embodiment of the present invention will now be described with reference to the drawings.

The gastrointestinal-tract constricting method of this embodiment differs from the first embodiment in that the method further includes a space forming step of forming a space between the mucosa basal layer M and the muscular layer P, the space forming step being performed between the identifying step S2 and the block forming step S3; and in that the block forming step S3 and supplying step S4 are performed while the mucosa basal layer M and the submucosal layer N are separated from each other. The inserting step S1, the identifying step S2, the endoscope withdrawing step S5, the waiting step S6, and the constriction confirming step S7 are the same as those in the first embodiment.

In the description of this embodiment, features common to the gastrointestinal-tract constricting method according to the first embodiment described above are denoted by the same reference signs, and descriptions therefor are omitted.

Figure 11:
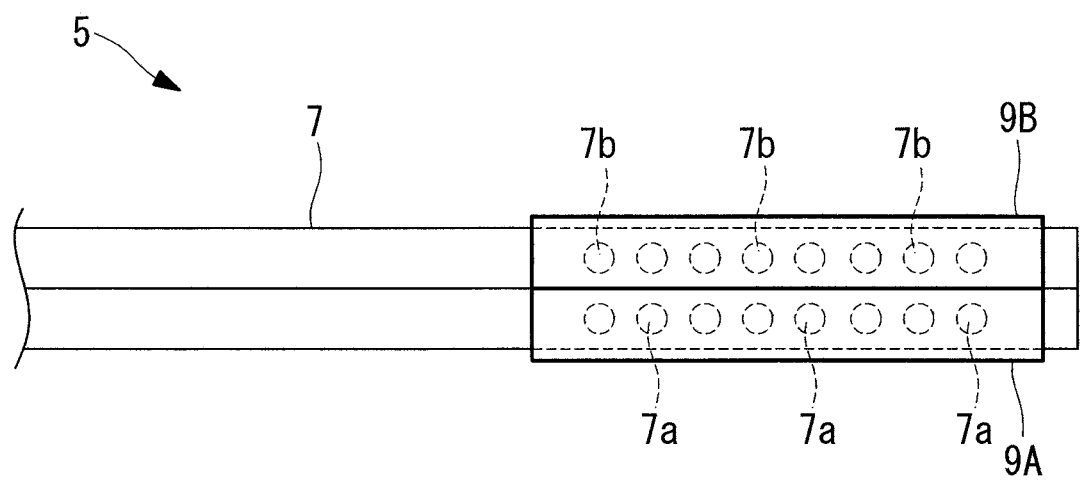
FIG. 11 is a plan view of a balloon catheter in a deflated-balloon state as viewed in the radial direction of a catheter body.
Figure 12:
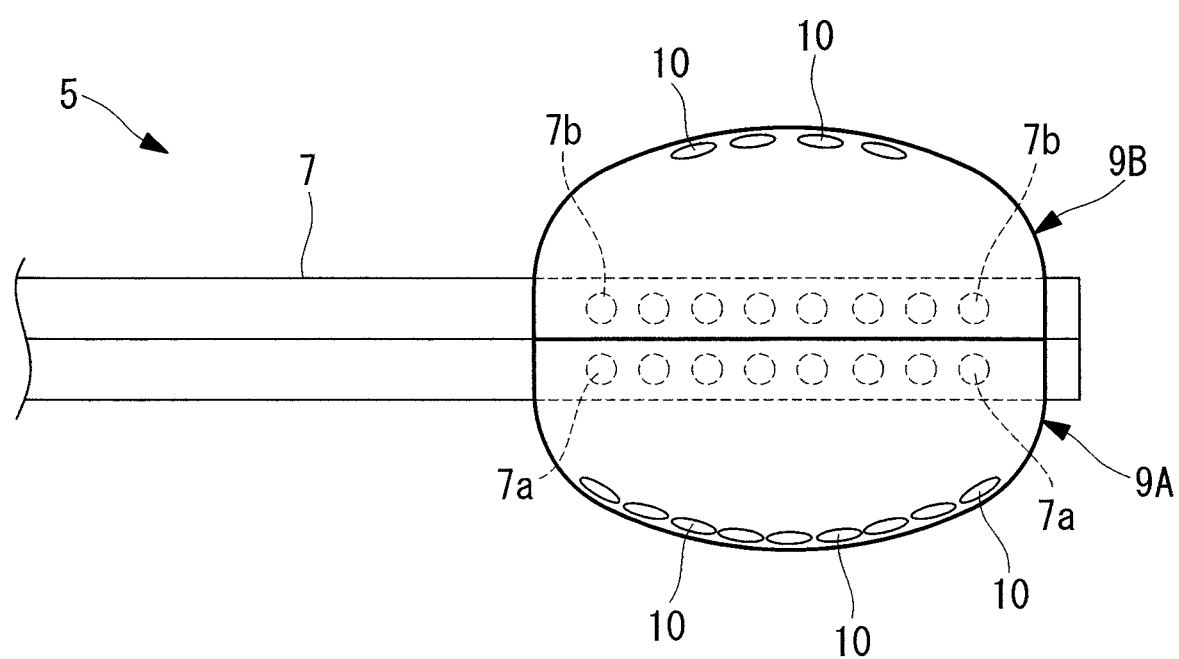
FIG. 12 is a plan view of the balloon catheter in an inflated-balloon state as viewed in the radial direction of the catheter body.

In the space forming step, for example, a space is formed inside the submucosal layer N by separating the submucosal layer N itself by using a balloon catheter (separating tool) 5, such as the one illustrated in FIGS. 11 and 12. Although an example in which the submucosal layer N itself is separated is described as an example in this embodiment, this example is not limiting. Alternatively, a space may be formed by performing separation at the boundary between the mucosa basal layer M and the submucosal layer N or the boundary between the submucosal layer N and the muscular layer P. The balloon catheter 5 is equipped with a catheter body 7, which has a thin long plate shape, and balloons 9A and 9B that are disposed in the distal end portion of the catheter body 7 and can be inflated and deflated in radial directions opposite from each other with the longitudinal axis of the catheter body 7 at the center.

The catheter body 7 is equipped with two lumens (none are illustrated in the drawings) that extend in the longitudinal direction inside the catheter body; one of the lumens has openings 7a in communication with the first balloon 9A and used for inflating the first balloon; and the other of the lumens has openings 7b in communication with the second balloon 9B and used for inflating the second balloon.

Figure 13:
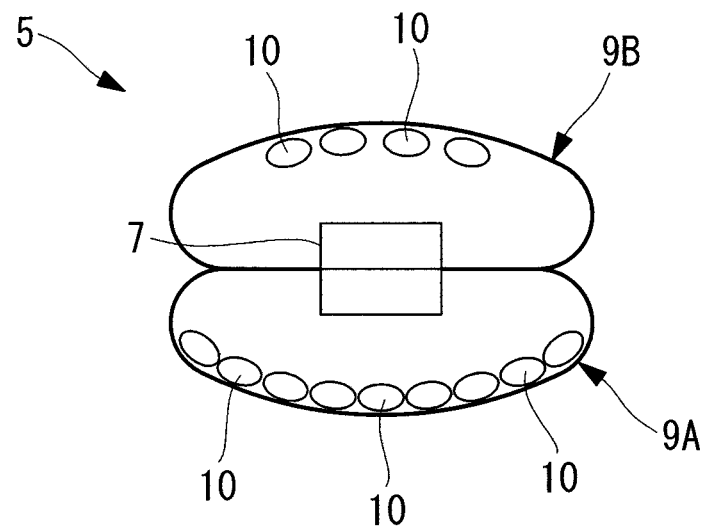
FIG. 13 is a plan view of a balloon under a pressure equal to or lower than a particular pressure value, as viewed in the radial direction of the catheter body.
Figure 14:
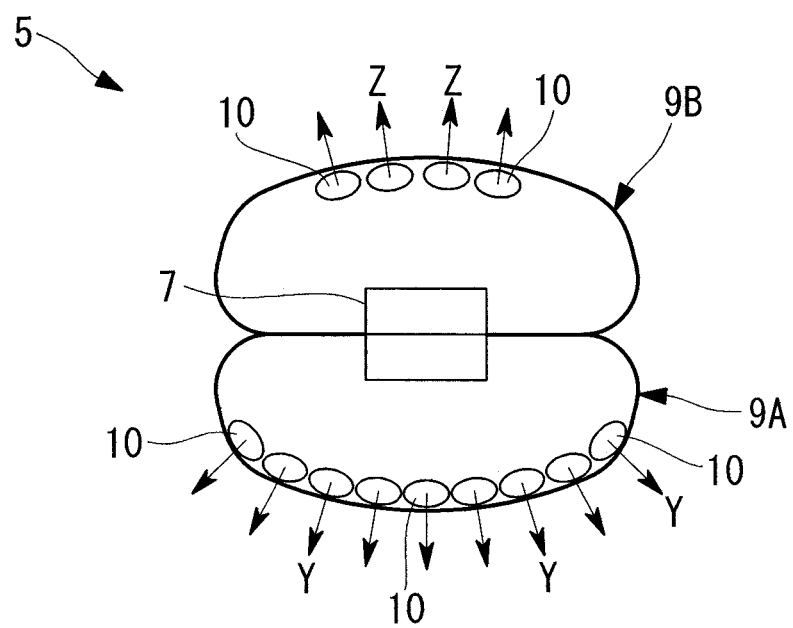
FIG. 14 is a plan view of a balloon under a pressure exceeding the particular pressure value, as viewed in the radial direction of the catheter body.

This balloon catheter 5 is configured such that, when pressure is applied to the lumens in the catheter body 7 by injecting liquids, the liquids fill the interiors of the balloons 9A and 9B through the balloon-inflating openings 7a and 7b, and, as illustrated in FIGS. 13 and 14, the balloons 9A and 9B inflate in opposite radial directions from each other with the longitudinal axis of the catheter body 7 at the center.

These balloons 9A and 9B have mesh portions 10 that open in the radial direction of the catheter body 7. The first balloon 9A has more mesh portions 10 than the second balloon 9B, and these mesh portions 10 are distributed over a wide range. The second balloon 9B has mesh portions 10 that are distributed over a range narrower than in the first balloon 9A.

In this balloon catheter 5, when the pressure applied to the balloons 9A and 9B is equal to or lower than a particular pressure value, the liquids filling the interiors of the inflated balloons 9A and 9B do not exude from the mesh portions 10, as illustrated in FIG. 13. In contrast, when the pressure applied to the balloons 9A and 9B exceeds the particular pressure value, the liquids filling the interiors of the inflated balloons 9A and 9B exude from the mesh portions 10, as illustrated in FIG. 14.

In the space forming step, the balloon catheter 5, with the balloons 9A and 9B in a deflated state, is inserted into the submucosal layer N in the target region R, and the balloons 9A and 9B are inflated by applying pressure from the interiors of the balloons 9A and 9B so as to tear the submucosal layer N and separate the interior of the submucosal layer N in the thickness direction (radial direction of the gastrointestinal tract), thereby forming a space inside the submucosal layer N.

In the block forming step S3 and the supplying step S4 of this embodiment, while the sodium hyaluronate solution Y is caused to exude from the mesh portions 10 of the first balloon 9A of the balloon catheter 5 pushed into the submucosal layer N in the space forming step and while the ethanol Z is caused to exude from the mesh portions 10 of the second balloon 9B, the balloon catheter 5 is withdrawn.

The effects of the gastrointestinal-tract constricting method according to this embodiment will now be described.

In order to constrict, for example, a part of the region that extends from the gastroesophageal junction H (lower part of the esophagus) to the cardiac part J of the subject with the gastrointestinal-tract constricting method of this embodiment, first, the endoscope 1 is inserted into the gastrointestinal tract in the inserting step S1, and, in the identifying step S2, the target region R is identified in the region that extends from the gastroesophageal junction H (lower part of the esophagus) to the cardiac part J.

Figure 15:
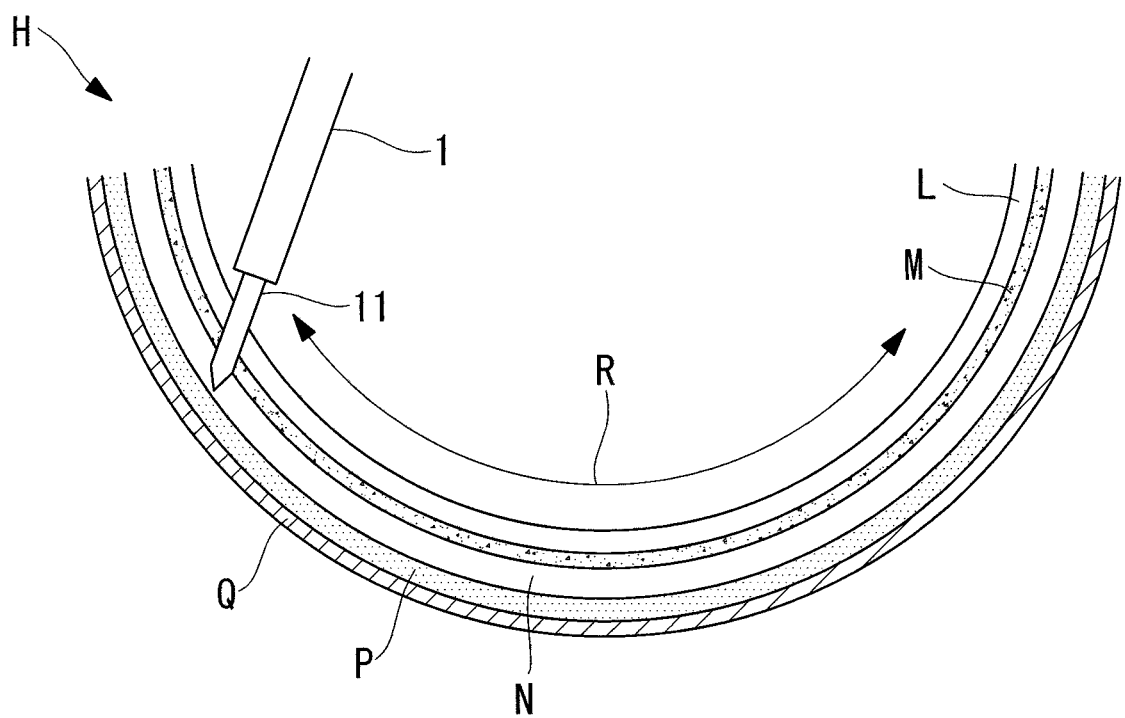
FIG. 15 is a partial cross-sectional view of the gastroesophageal junction taken along B-B' in FIG. 1, and illustrates how a catheter insertion hole, which penetrates from the mucosal layer to the submucosal layer in the target region, is formed by using an electrode-equipped treatment tool.
Figure 16:
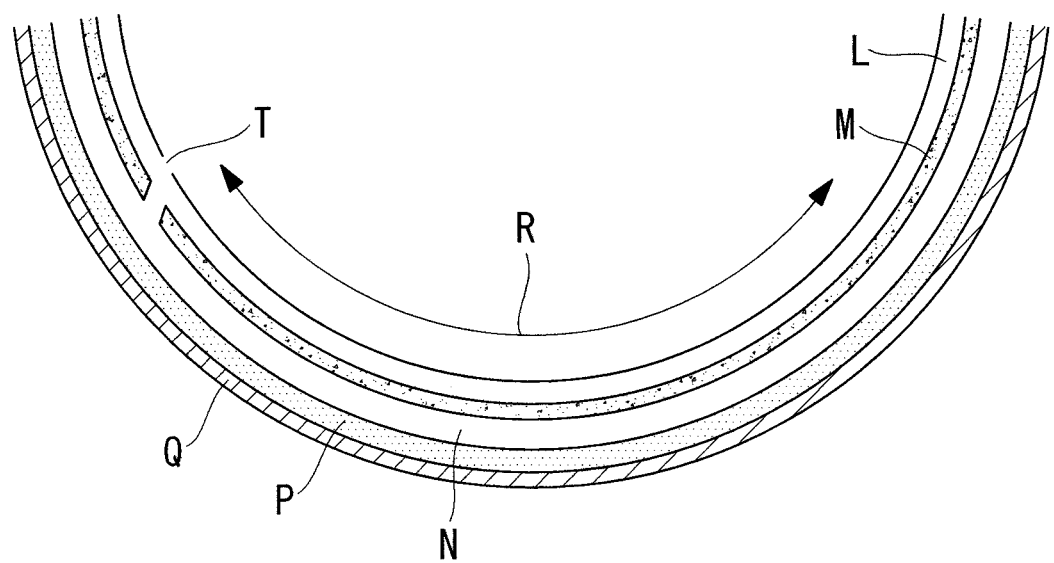
FIG. 16 is a partial cross-sectional view of the gastroesophageal junction taken along B-B' in FIG. 1, and illustrates the catheter insertion hole formed in the target region.

Next, as illustrated in FIGS. 15 and 16, first, an electrode-equipped treatment tool 11, which can, for example, excise biotissue with a high-frequency electrode, is inserted into a forceps channel of the endoscope 1 inserted into the gastrointestinal tract in the inserting step S1, and a catheter insertion hole T that penetrates from the surface of the mucosal layer L to the submucosal layer N is formed in one end of the target region R in the circumferential direction of the gastrointestinal tract.

Figure 17:
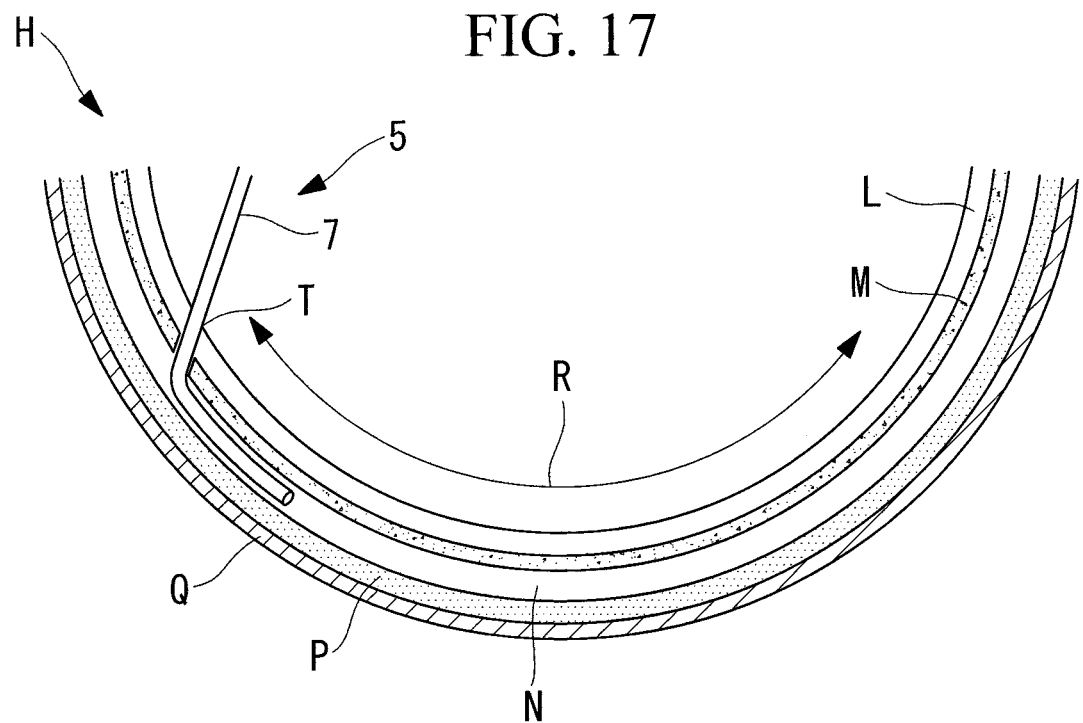
FIG. 17 is a partial cross-sectional view of the gastroesophageal junction taken along B-B' in FIG. 1, and illustrates how the balloon catheter is inserted into the submucosal layer through the catheter insertion hole.
Figure 18:
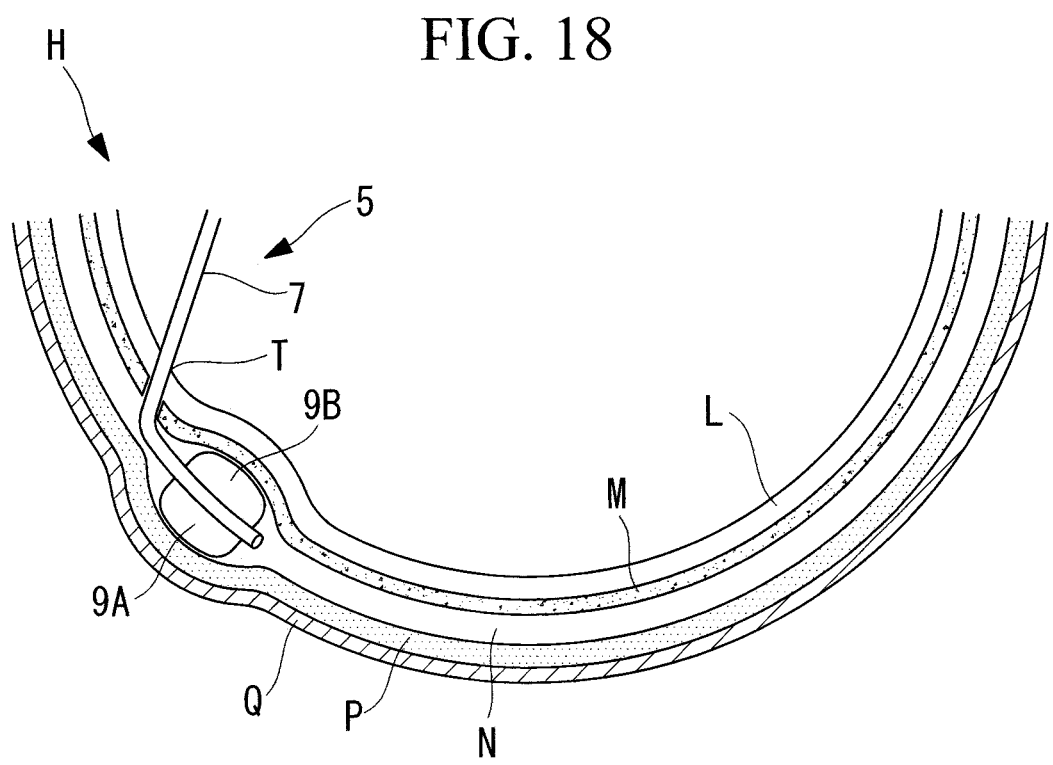
FIG. 18 is a partial cross-sectional view of the gastroesophageal junction taken along B-B' in FIG. 1, and illustrates how a balloon of the balloon catheter is inflated in the submucosal layer.

Next, as illustrated in FIG. 17, the balloon catheter 5 is inserted into the catheter insertion hole T. At this stage, the balloons 9A and 9B are in a deflated state. Then, while the balloons 9A and 9B are in a deflated state, the balloon catheter 5 is pushed into the interior of the submucosal layer N in the target region R. Subsequently, as illustrated in FIG. 18, the sodium hyaluronate solution Y is injected into the lumen in communication with the first balloon 9A so as to apply a pressure equal to or lower than the particular pressure value, and, at the same time, the ethanol Z is injected into the lumen in communication with the second balloon 9B so as to apply a pressure equal to or lower than the particular pressure value; as a result, the balloons 9A and 9B are inflated, and the submucosal layer N is partly separated in the radial direction of the gastrointestinal tract.

Figure 19:
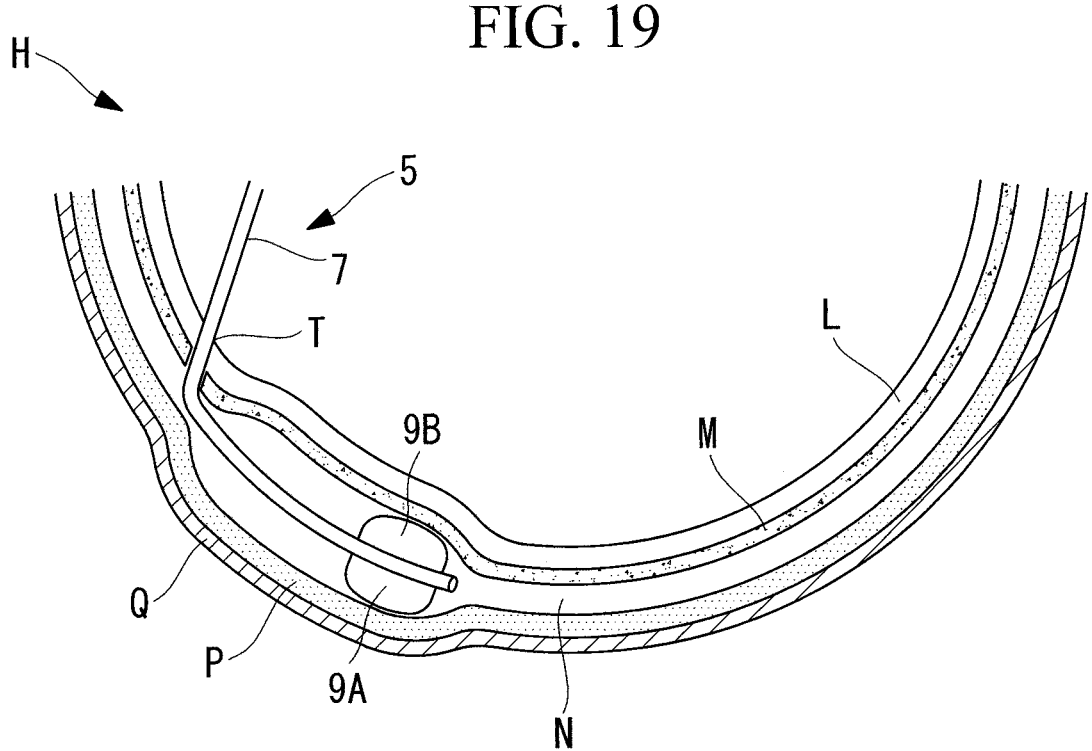
FIG. 19 is a partial cross-sectional view of the gastroesophageal junction taken along B-B' in FIG. 1, and illustrates how the balloon catheter is pushed along the submucosal layer.

Once the submucosal layer N is partly separated in the radial direction of the gastrointestinal tract, the balloons 9A and 9B are deflated again, and the balloon catheter 5 is further pushed into the interior of the unseparated part of the submucosal layer N. Subsequently, as illustrated in FIG. 19, the particular pressure value is again applied to inflate the balloons 9A and 9B so as to separate the interior of the submucosal layer N in the radial direction of the gastrointestinal tract. In this embodiment, the direction in which the balloon catheter 5 is pushed is the circumferential direction of the gastrointestinal tract that constitutes the gastroesophageal junction H, but the direction is not limited to this and may be the longitudinal direction of the gastrointestinal tract.

Figure 20:
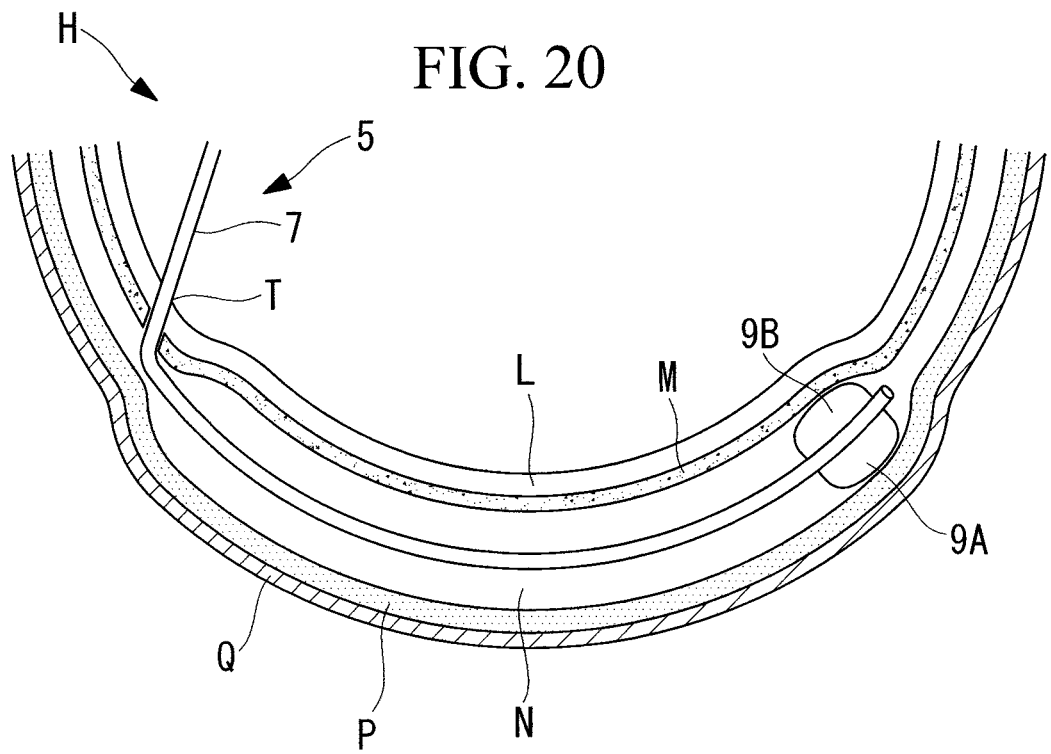
FIG. 20 is a partial cross-sectional view of the gastroesophageal junction taken along B-B' in FIG. 1, and illustrates the state in which the balloon catheter is pushed in so as to reach the other end of the target region in the circumferential direction of the gastroesophageal junction.

This operation is repeated, and, as illustrated in FIG. 20, the balloon catheter 5 is pushed until the balloon catheter 5 reaches the other end in the circumferential direction of the gastrointestinal tract that constitutes the target region R (for example, the gastroesophageal junction H) (space forming step). In this manner, the interior of the submucosal layer N from one end to the other end in the circumferential direction of the gastrointestinal tract that constitutes the target region R (for example, the gastroesophageal junction H) is separated in the radial direction of the gastrointestinal tract so as to form a space, which widens in the circumferential direction of the gastrointestinal tract, in the submucosal layer N. As a result, when the sodium hyaluronate solution Y is supplied to the submucosal layer N in the supplying step S4, the sodium hyaluronate solution Y can spread easily from one end to the other end in the circumferential direction of the gastrointestinal tract in the target region R (for example, the gastroesophageal junction H).

Figure 21:
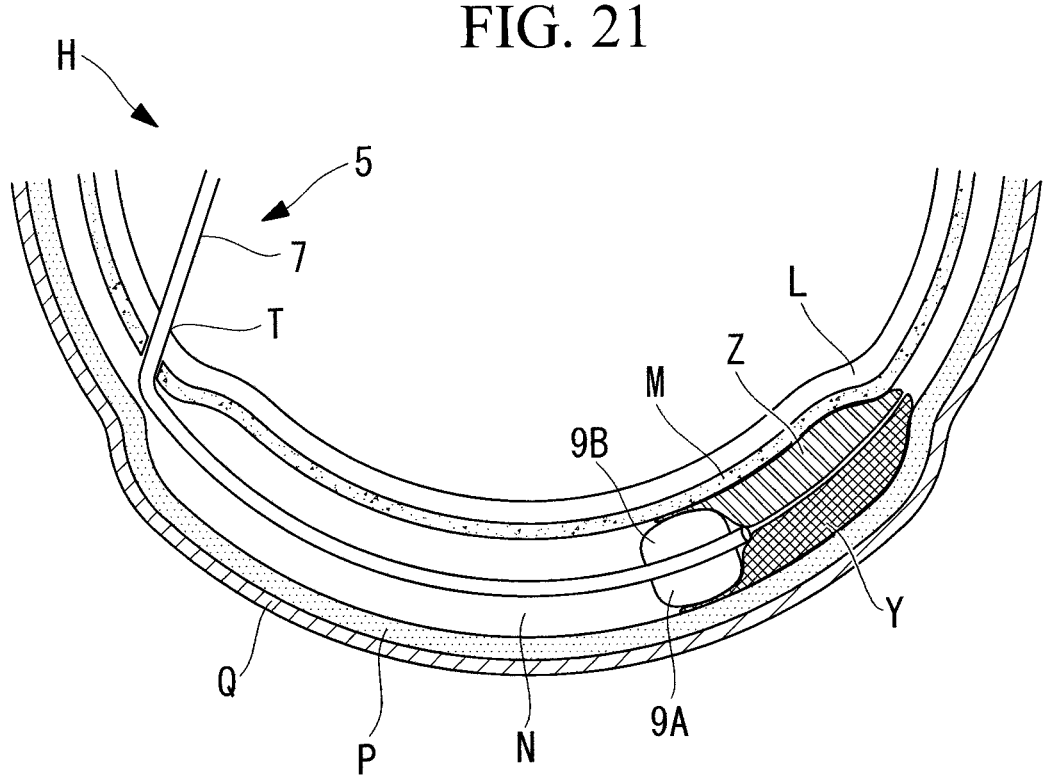
FIG. 21 is a partial cross-sectional view of the gastroesophageal junction taken along B-B' in FIG. 1, and illustrates how the balloon catheter is withdrawn while injecting a sodium hyaluronate solution and ethanol.

Next, as illustrated in FIG. 21, while a pressure exceeding the particular pressure value is applied to the balloons 9A and 9B so as to cause the sodium hyaluronate solution Y to exude from the mesh portions 10 of the first balloon 9A and to form a spreading block W formed of the sodium hyaluronate solution Y in the submucosal layer N and so as to cause the ethanol Z to exude from the mesh portions 10 of the second balloon 9B simultaneously, the balloon catheter 5 is withdrawn.

Figure 22:
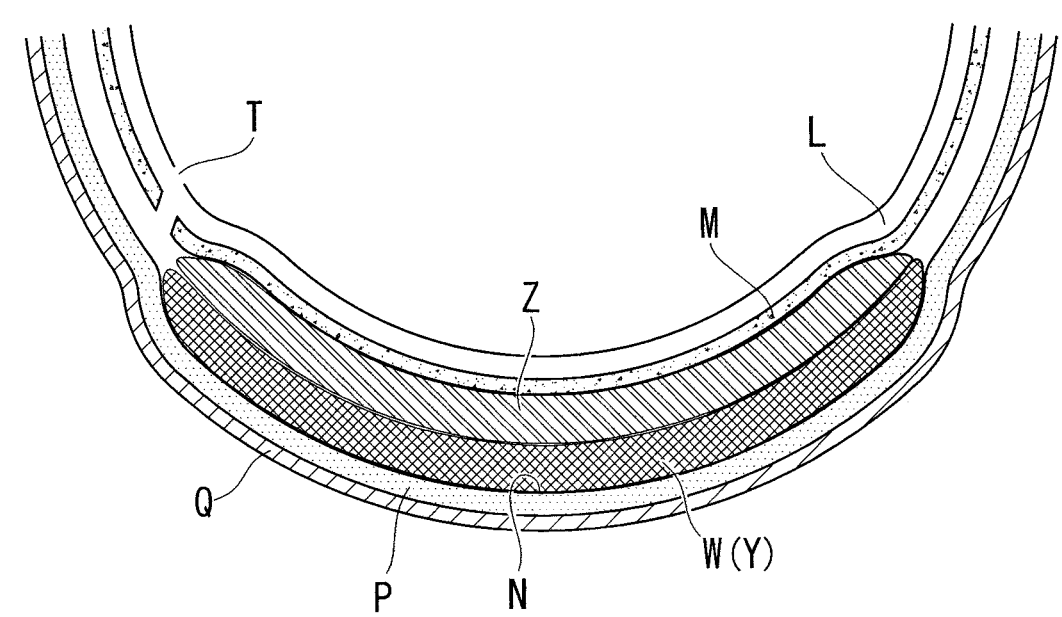
FIG. 22 is a partial cross-sectional view of the gastroesophageal junction taken along B-B' in FIG. 1, and illustrates the state in which the balloon catheter is withdrawn from the catheter insertion hole.

After the balloon catheter 5 is completely withdrawn from the catheter insertion hole T, as illustrated in FIG. 22, a spreading block W filled with the sodium hyaluronate solution Y is formed in the space formed in the submucosal layer N from one end to the other end in the circumferential direction of the gastrointestinal tract in the target region R (block forming step S3), and, at the same time, the ethanol Z is supplied between the spreading block W and the mucosa basal layer M (supplying step S4).

In this manner, while the ethanol Z damages the mucosa basal layer M in the target region R, infiltration of the ethanol Z into the muscular layer P and the radially outer side (abdominal cavity side) of the gastrointestinal tract with respect to the muscular layer P can be suppressed by the spreading block W.

As described above, with the gastrointestinal-tract constricting method according to this embodiment, the space and the spreading block W can be formed in the submucosal layer N, and the mucosa basal layer M can be damaged by the ethanol Z by performing insertion and removal operation of the balloon catheter 5 fewer times between the mucosa basal layer M and the muscular layer P, and thus the operation efficiency can be improved.

In addition, since the mesh portions 10 of the first balloon 9A, from which the sodium hyaluronate solution Y is exuded, are distributed over a wider range than the mesh portions 10 of the second balloon 9B, from which the ethanol Z is exuded, the sodium hyaluronate solution Y can be caused to exude over a wider range than the ethanol Z exuded simultaneously. In this manner, the spreading block W can be formed over a range wider than the range over which the ethanol Z is exuded, and, thus, infiltration of the ethanol Z circumventing the spreading block W into the muscular layer P side can be effectively suppressed.

In this embodiment, the sodium hyaluronate solution Y and the ethanol Z are simultaneously extracted; alternatively, after a space is formed by separating the interior of the submucosal layer N in the thickness direction, the balloon catheter 5 may be inserted and removed several times in that space so that, in the earlier insertion and removing operation, the sodium hyaluronate solution Y may be exuded to form a spreading block W in the space, and, in the later insertion and removing operation, the ethanol Z may be exuded along the surface of the spreading block on the side of the mucosa basal layer M in that space.

In this manner, since the spreading block W is formed first, infiltration of the ethanol Z into the muscular layer P side can be more reliably suppressed.

In this embodiment, the space is formed by separating the interior of the submucosal layer N in the circumferential direction of the gastrointestinal tract; alternatively, it suffices that a space that extends in the circumferential direction of the gastrointestinal tract can be formed between the mucosa basal layer M and the muscular layer P in the target region R. For example, separation may be performed at the boundary between the mucosa basal layer M and the submucosal layer N and along the circumferential direction of the gastrointestinal tract so that a space is formed between the mucosa basal layer M and the submucosal layer N. Alternatively, separation may be performed at the boundary between the submucosal layer N and the muscular layer P and along the circumferential direction of the gastrointestinal tract so that a space is formed between submucosal layer N and the muscular layer P. Alternatively, for example, in the region that extends from the gastroesophageal junction H (lower part of the esophagus) to the cardiac part J, the balloon catheter 5 may be inserted in the longitudinal direction of the gastrointestinal tract or in an oblique direction with respect to the longitudinal direction of the gastrointestinal tract so as to form a space between the mucosa basal layer M and the muscular layer P.

In this embodiment, both of the balloons 9A and 9B of the balloon catheter 5 are inflated in the submucosal layer N to separate the submucosal layer N in the radial direction of the gastrointestinal tract; alternatively, only one of the balloons 9A and 9B (for example, only the balloon 9A) may be inflated to separate the submucosal layer N in the radial direction of the gastrointestinal tract. The same applies to the case in which separation is performed at the boundary between the mucosa basal layer M and the submucosal layer N in the circumferential direction of the gastrointestinal tract, and to the case in which separation is performed at the boundary between the submucosal layer N and the muscular layer P in the circumferential direction of the gastrointestinal tract.

Although the balloon catheter 5 is used as an example of the separating tool in the description, the separating tool is not limited to this and may be any separating tool as long as a space can be formed between the mucosa basal layer M and the muscular layer P in the target region R.

Third Embodiment

A gastrointestinal-tract constricting method according to a third embodiment of the present invention will now be described with reference to the drawings.

The gastrointestinal-tract constricting method of this embodiment differs from the first embodiment in that, in the block forming step S3, the spreading block W is formed by using a sheet-shaped polylactate sheet (infiltration inhibitor sheet, refer to FIG. 25) E. The inserting step S1, the identifying step S2, the supplying step S4, the endoscope withdrawing step S5, the waiting step S6, and the constriction confirming step S7 are the same as those in the first embodiment.

In the description of this embodiment, features common to the gastrointestinal-tract constricting method according to the first embodiment described above are denoted by the same reference signs, and descriptions therefor are omitted.

Figure 23:
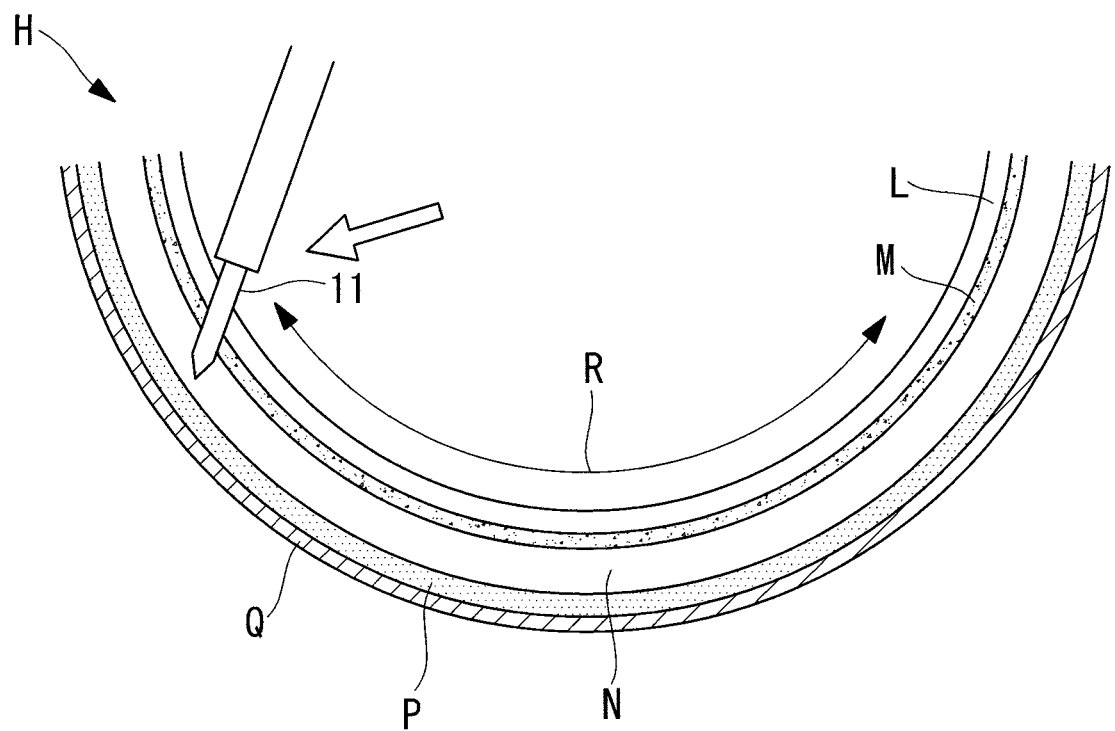
FIG. 23 is a partial cross-sectional view of the gastroesophageal junction taken along B-B' in FIG. 1, and illustrates how the electrode-equipped treatment tool incises the mucosal layer of the gastroesophageal junction.
Figure 24:
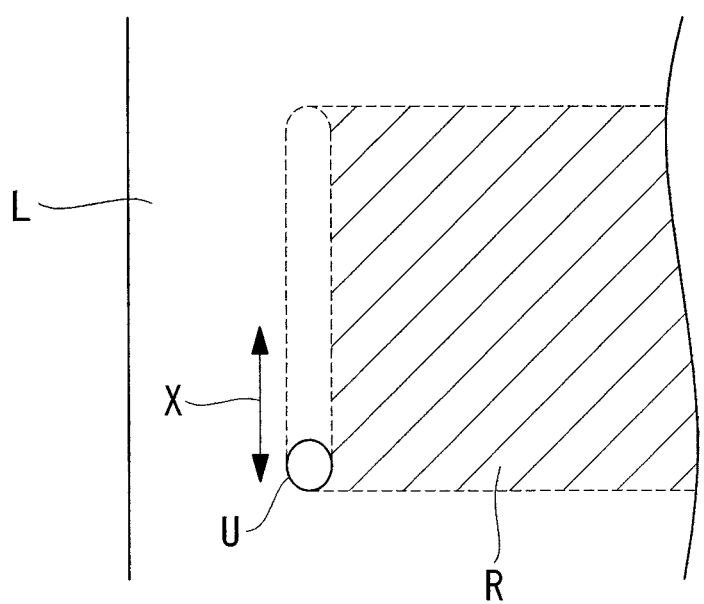
FIG. 24 is a plan view illustrating the incised portion of the mucosal layer.

In the block forming step S3 of this embodiment, the electrode-equipped treatment tool 11 is inserted into the forceps channel of the endoscope 1 inserted into the gastrointestinal tract in the inserting step S1, and, as illustrated in FIGS. 23 and 24, the mucosal layer L is incised at one end in the circumferential direction of the gastrointestinal tract constituting the target region R (for example, the gastroesophageal junction H) and along the longitudinal direction X of the gastrointestinal tract, so that the incised range is the same range as the target region R or a larger range than the target region R.

Figure 25:
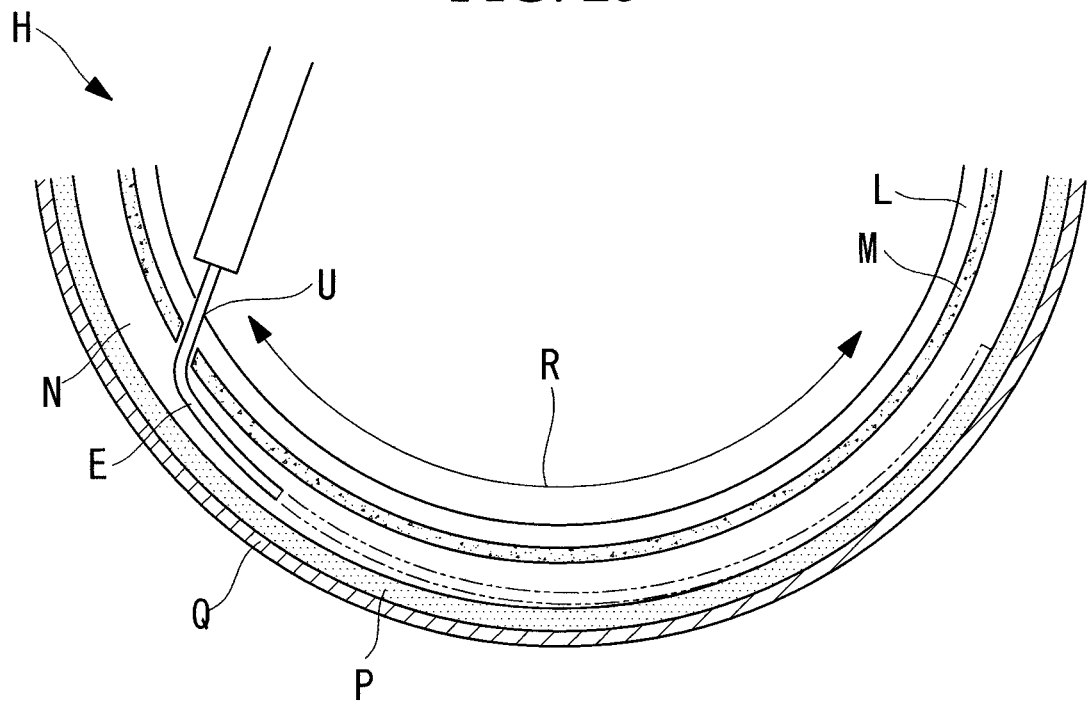
FIG. 25 is a partial cross-sectional view of the gastroesophageal junction taken along B-B' in FIG. 1, and illustrates how a polylactate sheet is inserted into the submucosal layer through the incised portion of the mucosal layer.
Figure 26:
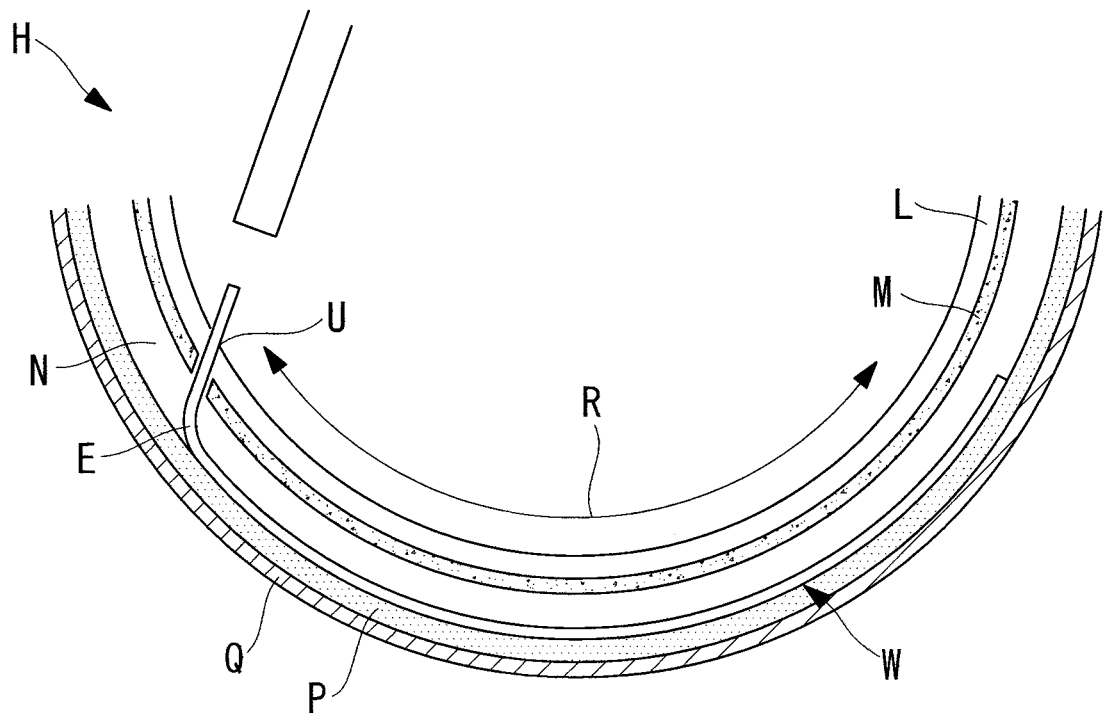
FIG. 26 is a partial cross-sectional view of the gastroesophageal junction taken along B-B' in FIG. 1, and illustrates how a spreading block formed of the polylactate sheet is formed in the submucosal layer.

Furthermore, in the block forming step S3, as illustrated in FIG. 25, the polylactate sheet E is inserted into the submucosal layer N from the incised portion U in the mucosal layer L, and the polylactate sheet E is pushed along the submucosal layer N until the polylactate sheet E passes the other end in the circumferential direction of the gastrointestinal tract in the target region R. Then, as illustrated in FIG. 26, the polylactate sheet E is placed in the submucosal layer N so as to form the spreading block W formed of the polylactate sheet E.

Figure 27:
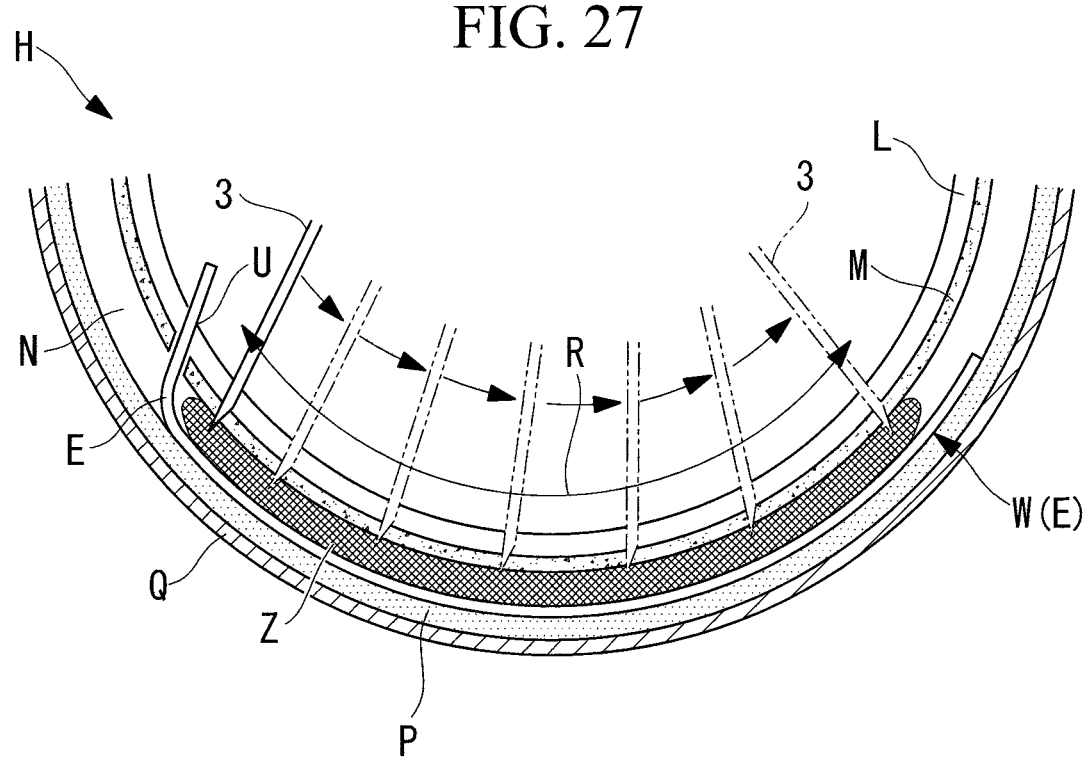
FIG. 27 is a partial cross-sectional view of the gastroesophageal junction taken along B-B' in FIG. 1, and illustrates how ethanol is injected between the spreading block and the mucosa basal layer.

In the supplying step S4, as illustrated in FIG. 27, the target region R is punctured with the injection needle 3 of the injection-needle-equipped treatment tool, and, within the range of the target region R (for example, the gastroesophageal junction H), the operation of injecting the ethanol Z between the spreading block W and the mucosa basal layer M is repeated several times while shifting the position within the target region R.

Figure 28:
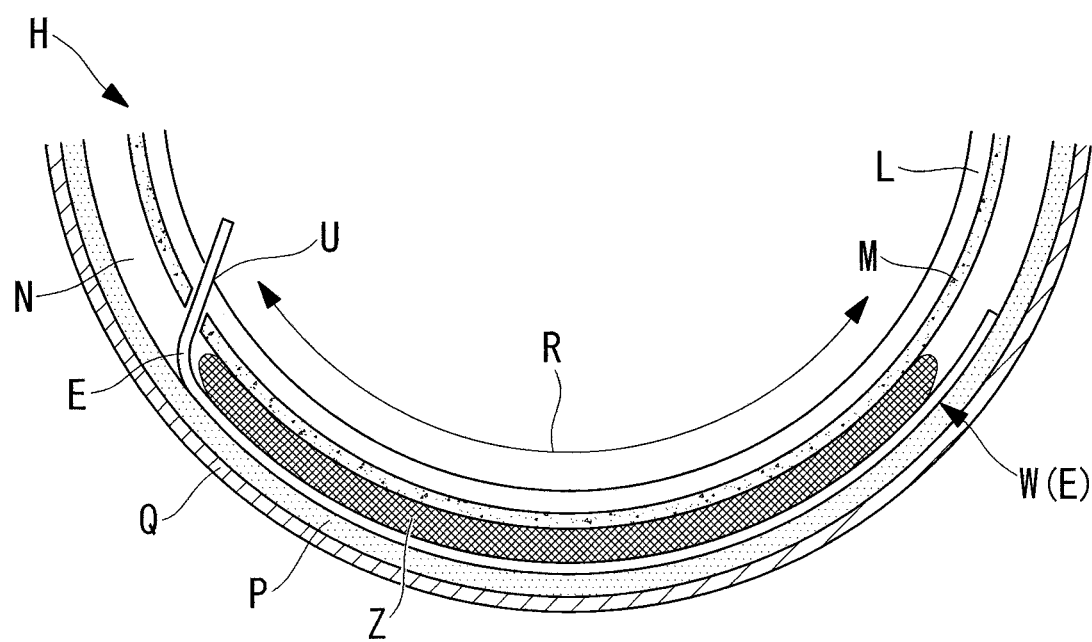
FIG. 28 is a partial cross-sectional view of the gastroesophageal junction taken along B-B' in FIG. 1, and illustrates how ethanol fills the space between the spreading block and the mucosa basal layer.

In this manner, as illustrated in FIG. 28, while the ethanol Z fills the space between the spreading block W and the mucosa basal layer M and damages the mucosa basal layer M in the target region R, infiltration of the ethanol Z into the muscular layer P and the radially outer side (abdominal cavity side) of the gastrointestinal tract with respect to the muscular layer P is suppressed by the spreading block W.

With the gastrointestinal-tract constricting method according to this embodiment, the spreading block W can be formed in the submucosal layer N by a single step of inserting the polylactate sheet E. In addition, by using the polylactate sheet E, which does not spread in the surrounding area within the submucosal layer N unlike a liquid infiltration inhibitor, the spreading block W can be formed in the desired region to serve as the infiltration inhibitor sheet. Since polylactate is decomposed into harmless substances inside the body, the polylactate sheet E can be left in the submucosal layer N, thus simplifying the procedure.

In this embodiment, the mucosal layer L is incised along the longitudinal direction X of the gastrointestinal tract that constitutes the target region R (for example, the gastroesophageal junction H), and the polylactate sheet E is inserted in the circumferential direction of the gastrointestinal tract; alternatively, for example, the mucosal layer L may be incised in the circumferential direction of the gastrointestinal tract, and the polylactate sheet E may be inserted in the longitudinal direction X of the gastrointestinal tract, or alternatively, the mucosal layer L may be incised obliquely with respect to the longitudinal direction X of the gastrointestinal tract, and the polylactate sheet E may be inserted obliquely with respect to the longitudinal direction X of the gastrointestinal tract.

Although ethanol Z is described as an example of the substance in the embodiments described above, the substance may be any substance that impairs the normal functions of cells, in other words, any substance that can damage cells, and examples thereof include, in addition to ethanol Z, peptase, protease, acetylcysteine, and sodium 2-mercaptoethanesulfonate.

Although the sodium hyaluronate solution Y is described as an example of the infiltration inhibitor in the first and second embodiments described above, the infiltration inhibitor may be any liquid that does not easily spread but remains at the position at which it is placed in the submucosal layer N, and examples thereof include, in addition to the sodium hyaluronate solution Y, sodium chondroitin sulfate, chitosan, poly-N-acetylglucosamine, carboxymethyl cellulose sodium, carmellose sodium, cyanoacrylate, and a polylactate sheet.

Among these substances and infiltration inhibitors, a combination of substances that are immiscible with each other, such as a combination of the ethanol Z and the sodium hyaluronate solution Y described above, may be used.

Although embodiments of the present invention have been described in detail with reference to the drawings in the description above, the specific structures are not limited to these embodiments and include design modifications etc., within the scope of the present invention. For example, the present invention is not limited to implementations in the embodiments and modifications described above but may be applied to embodiments in which these embodiments and modifications are appropriately combined, without specific limitation.

Although in the embodiments described above, the case in which the gastrointestinal-tract constricting method is applied to the treatment of gastroesophageal reflux disease is described, any approach with which the substance is supplied to the target region R of the gastrointestinal tract, and with which the gastrointestinal tract can be constricted by using the constrictive effect of the surrounding tissue in the target region R caused by formation of scars as the tissue in the damaged mucosa basal layer M heals will suffice. Thus, the application range is not limited to the treatment of gastroesophageal reflux disease, and the site where the method is to be applied is not limited to the gastroesophageal junction H or the region that extends from the gastroesophageal junction H (lower part of the esophagus) to the cardiac part J.

The following aspects of the invention are derived from the embodiments described above.

One aspect of the present invention provides a gastrointestinal-tract constricting method comprising: while observing the gastrointestinal tract by inserting an endoscope into the gastrointestinal tract, forming a spreading block that blocks infiltration of a substance, which damages a mucosa basal layer of the gastrointestinal tract, into the muscular layer underlying the mucosa basal layer, the spreading block being formed along a circumferential direction of the gastrointestinal tract and between the mucosa basal layer and the muscular layer; and supplying the substance to a gap between the spreading block and the mucosa basal layer while forming a contact surface between the spreading block and the substance along the circumferential direction of the gastrointestinal tract.

According to this aspect, the substance supplied is supplied to a position between the mucosal layer and the muscular layer of the gastrointestinal tract to damage the mucosa basal layer, and thus, the gastrointestinal tract can be constricted by utilizing the constrictive effect of the surrounding tissue undergoing scar formation as the damaged tissue heals.

In this case, the spreading block, which blocks infiltration of the substance into the muscular layer underlying the mucosa basal layer, is formed in advance between the mucosa basal layer and the muscular layer and along the circumferential direction of the gastrointestinal tract, and the substance is supplied to the gap between the spreading block and the mucosa basal layer while forming a contact surface between the spreading block and the substance along the circumferential direction of the gastrointestinal tract.; thus, the substance is blocked by the spreading block, and infiltration of the substance into the muscular layer on the outer side of the submucosal layer of the gastrointestinal tract can be suppressed.

Thus, the gastrointestinal tract can be constricted by causing the constrictive effect to occur in the tissue in the mucosa basal layer without damaging the muscular layer of the gastrointestinal tract.

In the aspect described above, the spreading block may be formed in a part of a region that extends from the gastroesophageal junction, where the stomach and the esophagus are joined, to the cardiac part.

When the spreading block is formed in a part of the region that extends from the gastroesophageal junction to the cardiac part, the part of the region that extends from the gastroesophageal junction to the cardiac part can be constricted without damaging the muscular layer of the gastroesophageal junction.

In the aspect described above, the spreading block may be formed over a range larger than a target region, which is a region where the mucosa basal layer is to be damaged by the substance, in the circumferential direction and a longitudinal direction of the gastrointestinal tract.

When the spreading block is formed over a range larger than the target region in the circumferential direction and the longitudinal direction of the gastrointestinal tract, infiltration of the substance, which circumvents the spreading block from the outer side in the circumferential direction of the gastrointestinal tract, into the muscular layer side can be suppressed.

In the aspect described above, the spreading block may be formed by inserting an injecting tool that injects an infiltration inhibitor, which suppresses infiltration of the substance, between the mucosa basal layer and the muscular layer and injecting the infiltration inhibitor.

By inserting the injecting tool into the submucosal layer and injecting the infiltration inhibitor through the injecting tool, the spreading block can be easily formed in the desired region between the mucosa basal layer and the muscular layer in a low invasive manner compared to the method that involves incising the gastrointestinal tract.

In the aspect described above, the infiltration inhibitor may be sodium hyaluronate, and the substance may be ethanol.

Sodium hyaluronate has a higher viscosity than ethanol, and sodium hyaluronate and ethanol are immiscible with each other. Thus, the spreading block can be easily and accurately formed in the desired region between the mucosa basal layer and the muscular layer by using sodium hyaluronate as the infiltration inhibitor, and infiltration of ethanol into the muscular layer side can be effectively suppressed by the spreading block formed of sodium hyaluronate.

In the aspect described above, a space may be formed between the mucosa basal layer and the muscular layer by inserting a separating tool between the mucosa basal layer and the muscular layer, and, while maintaining a state in which the space is formed between the mucosa basal layer and the muscular layer, an infiltration inhibitor, which suppresses infiltration of the substance, may be supplied to the space so as to form the spreading block, and, at the same time, the substance may be supplied within the space and along the surface of the spreading block on the side of the mucosa basal layer.

When the separating tool is inserted between the mucosa basal layer and the muscular layer and the space is formed between the mucosa basal layer and the muscular layer in advance, the spreading block can be easily and more reliably formed between the mucosa basal layer and the muscular layer, and the substance can be supplied to the gap along the surface of the spreading block on the side of the mucosa basal layer.

In the aspect described above, the separating tool may be formed to be capable of extracting the infiltration inhibitor, and, while the infiltration inhibitor is supplied to the space from the separating tool, the separating tool inserted into the space may be withdrawn.

When the separating tool is withdrawn from the space while the infiltration inhibitor is supplied to the space from the separating tool, fewer operation steps of inserting and removing the separating tool between the mucosa basal layer and the muscular layer are required to form the space and the spreading block between the mucosa basal layer and the muscular layer, and the operation efficiency can be improved.

In the aspect described above, the separating tool may be formed to be capable of extracting the substance also, and, while the infiltration inhibitor is supplied in the space from the separating tool to form the spreading block, the substance may be supplied along the surface of the spreading block on the side of the mucosa basal layer, and, at the same time, the separating tool inserted into the space may be withdrawn.

When the separating tool is withdrawn from the space while the infiltration inhibitor is supplied to the space from the separating tool to form the spreading block and while the substance is supplied along the surface of the spreading block on the side of the mucosa basal layer, fewer operation steps of inserting and removing the separating tool between the mucosa basal layer and the muscular layer are required to form the space and the spreading block between the mucosa basal layer and the muscular layer, and, at the same time, the mucosa basal layer can be damaged by the substance. Thus, the operation efficiency can be further improved.

In the aspect described above, the infiltration inhibitor may be sodium hyaluronate, and the substance may be ethanol.

In the aspect described above, a mucosal layer may be incised, and a sheet-shaped infiltration inhibitor sheet that suppresses infiltration of the substance may be inserted from the incised portion of the mucosal layer and placed between the mucosa basal layer and the muscular layer so as to form the spreading block.

When the infiltration inhibitor sheet is inserted from the incised portion of the mucosal layer and placed between the mucosa basal layer and the muscular layer, the spreading block can be formed between the mucosa basal layer and the muscular layer by a single step of inserting the infiltration inhibitor sheet. In addition, by using the sheet-shaped infiltration inhibitor sheet, the spreading block can be formed in the desired region in a manner unlike the case of using the liquid infiltration inhibitor, which spreads in the surrounding area between the mucosa basal layer and the muscular layer.

In the aspect described above, the infiltration inhibitor sheet may be composed of polylactate, and the substance may be ethanol.

Since polylactate is decomposed into harmless substances inside the body, the infiltration inhibitor sheet can be left between the mucosa basal layer and the muscular layer, and thus the procedure can be facilitated.

REFERENCE SIGNS LIST 1 endoscope
5 balloon catheter (separating tool)
E polylactate sheet (infiltration inhibitor sheet)
H gastroesophageal junction (gastrointestinal tract)
R target region
W spreading block
Y sodium hyaluronate solution (infiltration inhibitor)
Z ethanol (substance)

The invention claimed is:

1. A gastrointestinal-tract constricting method comprising:
    while observing the gastrointestinal tract by inserting an endoscope into the gastrointestinal tract, forming a spreading block that blocks infiltration of a substance, which damages a mucosa basal layer of the gastrointestinal tract, into the muscular layer underlying the mucosa basal layer, the spreading block being formed along a circumferential direction of the gastrointestinal tract and between the mucosa basal layer and the muscular layer; and
    supplying the substance to a gap between the spreading block and the mucosa basal layer while forming a contact surface between the spreading block and the substance along the circumferential direction of the gastrointestinal tract.

2. The gastrointestinal-tract constricting method according to claim 1, wherein the spreading block is formed in a part of a region that extends from the gastroesophageal junction, where the stomach and the esophagus are joined, to the cardiac part.

3. The gastrointestinal-tract constricting method according to claim 1, wherein the spreading block is formed over a range larger than a target region, which is a region where the mucosa basal layer is to be damaged by the substance, in the circumferential direction and a longitudinal direction of the gastrointestinal tract.

4. The gastrointestinal-tract constricting method according to claim 1, wherein the spreading block is formed by inserting an injecting tool that injects an infiltration inhibitor, which suppresses infiltration of the substance, between the mucosa basal layer and the muscular layer and injecting the infiltration inhibitor.

5. The gastrointestinal-tract constricting method according to claim 4, wherein the infiltration inhibitor is sodium hyaluronate and the substance is ethanol.

6. The gastrointestinal-tract constricting method according to claim 1, wherein:
    a space is formed between the mucosa basal layer and the muscular layer by inserting a separating tool between the mucosa basal layer and the muscular layer, and
    while maintaining a state in which the space is formed between the mucosa basal layer and the muscular layer, an infiltration inhibitor, which suppresses infiltration of the substance, is supplied to the space so as to form the spreading block, and, at the same time, the substance is supplied within the space and along the surface of the spreading block on the side of the mucosa basal layer.

7. The gastrointestinal-tract constricting method according to claim 6, wherein:
    the separating tool is formed to be capable of extracting the infiltration inhibitor, and
    while the infiltration inhibitor is supplied to the space from the separating tool, the separating tool inserted into the space is withdrawn.

8. The gastrointestinal-tract constricting method according to claim 7, wherein:
    the separating tool is formed to be capable of extracting the substance also, and
    while the infiltration inhibitor is supplied in the space from the separating tool to form the spreading block, the substance is supplied along the surface of the spreading block on the side of the mucosa basal layer, and, at the same time, the separating tool inserted into the space is withdrawn.

9. The gastrointestinal-tract constricting method according to claim 6, wherein:
the infiltration inhibitor is sodium hyaluronate and the substance is ethanol.

10. The gastrointestinal-tract constricting method according to claim 1, wherein a mucosa layer is incised, and a sheet-shaped infiltration inhibitor sheet that suppresses infiltration of the substance is inserted from the incised portion of the mucosa layer and placed between the mucosa basal layer and the muscular layer so as to form the spreading block.

11. The gastrointestinal-tract constricting method according to claim 10, wherein:
the infiltration inhibitor sheet is composed of polylactate, and the substance is ethanol.

* * * * *